US011487138B2

(12) United States Patent
Blum et al.

(10) Patent No.: US 11,487,138 B2
(45) Date of Patent: Nov. 1, 2022

(54) EYEWEAR DOCKING STATION AND ELECTRONIC MODULE

(71) Applicant: e-Vision Smart Optics, Inc., Sarasota, FL (US)

(72) Inventors: Ronald Blum, Roanoke, VA (US); Yongping Wang, Philadelphia, PA (US); Mark Graham, Roanoke, VA (US); William Kokonaski, Gig Harbor, WA (US); Richard Clompus, Roanoke, VA (US)

(73) Assignee: e-Vision Smart Optics, Inc., Sarasota, FL (US)

( * ) Notice: Subject to any disclaimer, the term of this patent is extended or adjusted under 35 U.S.C. 154(b) by 386 days.

(21) Appl. No.: 16/819,262

(22) Filed: Mar. 16, 2020

(65) Prior Publication Data
US 2020/0218093 A1    Jul. 9, 2020

Related U.S. Application Data

(63) Continuation of application No. 15/975,353, filed on May 9, 2018, now Pat. No. 10,598,960, which is a
(Continued)

(51) Int. Cl.
*G02C 11/00* (2006.01)
*G02C 11/06* (2006.01)
(Continued)

(52) U.S. Cl.
CPC .............. *G02C 11/10* (2013.01); *G02C 7/081* (2013.01); *G02C 11/04* (2013.01); *G02C 11/06* (2013.01);
(Continued)

(58) Field of Classification Search
CPC ........ G02C 7/081; G02C 11/10; G02C 11/04; G02C 11/06; G05B 15/02; A61F 9/061; G06K 19/0715; G06K 19/07762
(Continued)

(56) References Cited

U.S. PATENT DOCUMENTS 2,170,287 A    8/1939 Kinnebrew
2,437,642 A    3/1948 Henroteau
(Continued)

FOREIGN PATENT DOCUMENTS

CN    89113088 A    10/2001
CN    2911723 Y     6/2007
(Continued)

OTHER PUBLICATIONS

Supplemental Notice of Allowance in U.S. Appl. No. 13/779,407, dated Nov. 12, 2014, 2 pages.
(Continued)

*Primary Examiner* — William R Alexander
(74) *Attorney, Agent, or Firm* — Smith Baluch LLP

(57) ABSTRACT

An eyewear system including an eyewear frame and an application module. The eyewear frame including a docking station, and an electronic connector including a first set of preconfigured application connection points. The application module adapted to be mounted to the docking station, and including an electronic device configured to perform a function, and a second set of preconfigured application connection points corresponding to at least some of the first set of preconfigured application connection points. The second set of preconfigured application connection points including at least two different sub-function connections used to support the function of the electronic device.

20 Claims, 15 Drawing Sheets

Related U.S. Application Data continuation of application No. 14/808,239, filed on Jul. 24, 2015, now Pat. No. 10,114,235, which is a continuation of application No. 13/735,887, filed on Jan. 7, 2013, now Pat. No. 9,122,083.

(60) Provisional application No. 61/640,425, filed on Apr. 30, 2012, provisional application No. 61/638,150, filed on Apr. 25, 2012, provisional application No. 61/622,092, filed on Apr. 10, 2012, provisional application No. 61/583,940, filed on Jan. 6, 2012.

(51) Int. Cl.

| | | |
|---|---|---|
| G02C 7/08 | (2006.01) | |
| G02C 11/04 | (2006.01) | |
| G05B 15/02 | (2006.01) | |
| G06K 19/07 | (2006.01) | |
| G06K 19/077 | (2006.01) | |
| A61F 9/06 | (2006.01) | |

(52) U.S. Cl.
CPC ......... *G05B 15/02* (2013.01); *G06K 19/0715* (2013.01); *G06K 19/07762* (2013.01); *A61F 9/061* (2013.01)

(58) Field of Classification Search
USPC ....................................................... 351/158
See application file for complete search history.

(56) References Cited

U.S. PATENT DOCUMENTS

| | | |
|---|---|---|
| 2,576,581 A | 11/1951 | Edwards |
| 3,161,718 A | 12/1964 | De Luca |
| 3,183,523 A | 5/1965 | Harrison |
| 3,245,315 A | 4/1966 | Marks et al. |
| 3,248,460 A | 4/1966 | Naujokas |
| 3,309,162 A | 3/1967 | Kosanke et al. |
| 3,614,215 A | 10/1971 | Leo |
| 3,738,734 A | 6/1973 | Tait et al. |
| 3,791,719 A | 2/1974 | Kratzer et al. |
| 4,050,814 A | 9/1977 | Mcfadden |
| 4,062,629 A | 12/1977 | Winthrop |
| 4,174,156 A | 11/1979 | Glorieux |
| 4,181,408 A | 1/1980 | Senders |
| 4,190,330 A | 2/1980 | Berreman |
| 4,190,621 A | 2/1980 | Greshes |
| 4,257,691 A | 3/1981 | Brooks |
| 4,264,154 A | 4/1981 | Petersen |
| 4,279,474 A | 7/1981 | Belgorod |
| 4,300,818 A | 11/1981 | Schachar |
| 4,320,939 A | 3/1982 | Mueller |
| 4,373,218 A | 2/1983 | Schachar |
| 4,395,736 A | 7/1983 | Fraleux |
| 4,418,990 A | 12/1983 | Gerber |
| 4,423,929 A | 1/1984 | Gomi |
| 4,457,585 A | 7/1984 | Ducorday |
| 4,461,550 A | 7/1984 | Legendre |
| 4,461,629 A | 7/1984 | Arisaki |
| 4,466,703 A | 8/1984 | Nishimoto |
| 4,466,706 A | 8/1984 | Lamothe, II |
| 4,529,268 A | 7/1985 | Brown |
| 4,564,267 A | 1/1986 | Nishimoto |
| 4,572,616 A | 2/1986 | Kowel et al. |
| 4,577,928 A | 3/1986 | Brown |
| 4,601,545 A | 7/1986 | Kern |
| 4,609,824 A | 9/1986 | Munier et al. |
| 4,712,870 A | 12/1987 | Robinson et al. |
| 4,753,514 A | 6/1988 | Kubik |
| 4,756,605 A | 7/1988 | Okada et al. |
| 4,772,094 A | 9/1988 | Sheiman |
| D298,250 S | 10/1988 | Kildall |
| 4,781,440 A | 11/1988 | Toda |
| 4,787,733 A | 11/1988 | Silva |
| 4,787,903 A | 11/1988 | Grendahl |
| 4,795,248 A | 1/1989 | Okada et al. |
| 4,813,777 A | 3/1989 | Rainville et al. |
| 4,816,031 A | 3/1989 | Pfoff |
| 4,818,095 A | 4/1989 | Takeuchi |
| 4,836,652 A | 6/1989 | Oishi et al. |
| 4,842,400 A | 6/1989 | Klein |
| 4,869,588 A | 9/1989 | Frieder et al. |
| 4,873,029 A | 10/1989 | Blum |
| 4,880,300 A | 11/1989 | Payner et al. |
| 4,890,903 A | 1/1990 | Treisman et al. |
| 4,904,063 A | 2/1990 | Okada et al. |
| 4,907,860 A | 3/1990 | Noble |
| 4,909,626 A | 3/1990 | Purvis et al. |
| 4,919,520 A | 4/1990 | Okada et al. |
| 4,921,728 A | 5/1990 | Takiguchi et al. |
| 4,927,241 A | 5/1990 | Kuijk |
| 4,929,865 A | 5/1990 | Blum |
| 4,930,884 A | 6/1990 | Tichenor et al. |
| 4,944,584 A | 7/1990 | Maeda et al. |
| 4,945,242 A | 7/1990 | Berger et al. |
| 4,952,048 A | 8/1990 | Frieder et al. |
| 4,952,788 A | 8/1990 | Berger et al. |
| 4,955,712 A | 9/1990 | Barth et al. |
| 4,958,907 A | 9/1990 | Davis |
| 4,961,639 A | 10/1990 | Lazarus |
| 4,968,127 A | 11/1990 | Russell et al. |
| 4,981,342 A | 1/1991 | Fiala |
| 4,991,951 A | 2/1991 | Mizuno et al. |
| 5,015,086 A | 5/1991 | Okaue et al. |
| 5,030,882 A | 7/1991 | Solero |
| 5,050,981 A | 9/1991 | Roffman |
| 5,066,301 A | 11/1991 | Wiley |
| 5,067,795 A | 11/1991 | Senatore |
| 5,073,021 A | 12/1991 | Marron |
| 5,076,665 A | 12/1991 | Petersen |
| 5,089,023 A | 2/1992 | Swanson |
| 5,091,801 A | 2/1992 | Ebstein |
| 5,108,169 A | 4/1992 | Mandell |
| 5,114,628 A | 5/1992 | Hoefer et al. |
| 5,130,856 A | 7/1992 | Tichenor et al. |
| 5,142,411 A | 8/1992 | Fiala |
| 5,147,585 A | 9/1992 | Blum |
| 5,150,234 A | 9/1992 | Takahashi et al. |
| 5,171,266 A | 12/1992 | Wiley et al. |
| 5,173,723 A | 12/1992 | Volk |
| 5,178,800 A | 1/1993 | Blum |
| 5,182,585 A | 1/1993 | Stoner |
| 5,184,156 A | 2/1993 | Black et al. |
| 5,200,859 A | 4/1993 | Payner et al. |
| 5,208,688 A | 5/1993 | Fergason et al. |
| 5,219,497 A | 6/1993 | Blum |
| 5,229,797 A | 7/1993 | Futhey et al. |
| 5,229,885 A | 7/1993 | Quaglia |
| 5,231,430 A | 7/1993 | Kohayakawa |
| 5,239,412 A | 8/1993 | Naka et al. |
| D342,063 S | 12/1993 | Howitt et al. |
| 5,305,028 A | 4/1994 | Okano |
| 5,306,926 A | 4/1994 | Yonemoto |
| 5,324,930 A | 6/1994 | Jech |
| D350,342 S | 9/1994 | Sack |
| 5,352,886 A | 10/1994 | Kane |
| 5,359,444 A | 10/1994 | Piosenka et al. |
| 5,375,006 A | 12/1994 | Haas |
| 5,382,986 A | 1/1995 | Black et al. |
| 5,386,308 A | 1/1995 | Michel et al. |
| 5,411,537 A | 5/1995 | Munshi et al. |
| 5,424,927 A | 6/1995 | Schaller et al. |
| 5,440,357 A | 8/1995 | Quaglia |
| 5,443,506 A | 8/1995 | Garabet |
| 5,451,766 A | 9/1995 | Van |
| 5,455,638 A | 10/1995 | Kallman et al. |
| 5,488,439 A | 1/1996 | Weltmann |
| 5,512,371 A | 4/1996 | Gupta et al. |
| 5,522,323 A | 6/1996 | Richard |
| 5,552,841 A | 9/1996 | Gallorini et al. |
| 5,585,871 A | 12/1996 | Linden |
| 5,606,743 A | 2/1997 | Vogt et al. |
| 5,608,567 A | 3/1997 | Grupp |

(56) References Cited

U.S. PATENT DOCUMENTS

| | | |
|---|---|---|
| 5,608,808 A | 3/1997 | Da |
| 5,615,588 A | 4/1997 | Gottschald |
| 5,653,751 A | 8/1997 | Samiy et al. |
| 5,654,786 A | 8/1997 | Gerald |
| 5,668,620 A | 9/1997 | Kurtin et al. |
| 5,682,223 A | 10/1997 | Menezes et al. |
| 5,683,457 A | 11/1997 | Gupta et al. |
| RE35,691 E | 12/1997 | Theirl et al. |
| 5,702,819 A | 12/1997 | Gupta et al. |
| 5,712,721 A | 1/1998 | Large |
| 5,715,337 A | 2/1998 | Spitzer et al. |
| 5,728,155 A | 3/1998 | Anello et al. |
| 5,739,959 A | 4/1998 | Quaglia |
| 5,757,458 A | 5/1998 | Miller et al. |
| 5,777,719 A | 7/1998 | Williams et al. |
| 5,815,233 A | 9/1998 | Morokawa et al. |
| 5,815,239 A | 9/1998 | Chapman et al. |
| 5,859,685 A | 1/1999 | Gupta et al. |
| 5,861,934 A | 1/1999 | Blum et al. |
| 5,861,936 A | 1/1999 | Sorensen |
| 5,877,876 A | 3/1999 | Birdwell |
| 5,900,720 A | 5/1999 | Kallman et al. |
| 5,905,561 A | 5/1999 | Lee et al. |
| 5,949,521 A | 9/1999 | Williams et al. |
| 5,953,098 A | 9/1999 | Lieberman et al. |
| 5,956,183 A | 9/1999 | Epstein et al. |
| 5,963,300 A | 10/1999 | Horwitz |
| 5,971,540 A | 10/1999 | Ofner |
| 5,980,037 A | 11/1999 | Conway |
| 5,988,816 A | 11/1999 | Quadri |
| 5,999,328 A | 12/1999 | Kurtin et al. |
| 6,040,947 A | 3/2000 | Kurtin et al. |
| 6,050,687 A | 4/2000 | Bille et al. |
| 6,069,742 A | 5/2000 | Silver |
| 6,086,203 A | 7/2000 | Blum et al. |
| 6,086,204 A | 7/2000 | Magnante |
| 6,091,546 A | 7/2000 | Spitzer |
| 6,091,832 A | 7/2000 | Shurman et al. |
| 6,095,651 A | 8/2000 | Williams et al. |
| 6,099,117 A | 8/2000 | Gregory |
| 6,115,177 A | 9/2000 | Vossler |
| 6,139,148 A | 10/2000 | Menezes |
| 6,145,987 A | 11/2000 | Baude et al. |
| 6,157,291 A | 12/2000 | Kuenster et al. |
| 6,165,123 A | 12/2000 | Thompson |
| 6,184,847 B1 | 2/2001 | Fateh et al. |
| 6,188,525 B1 | 2/2001 | Silver |
| 6,191,881 B1 | 2/2001 | Tajima |
| 6,199,984 B1 | 3/2001 | Menezes |
| 6,199,986 B1 | 3/2001 | Williams et al. |
| 6,204,974 B1 | 3/2001 | Spitzer |
| 6,213,602 B1 | 4/2001 | Smarto |
| 6,270,220 B1 | 8/2001 | Keren |
| 6,271,915 B1 | 8/2001 | Frey et al. |
| 6,282,449 B1 | 8/2001 | Kamerling et al. |
| 6,299,311 B1 | 10/2001 | Williams et al. |
| 6,305,802 B1 | 10/2001 | Roffman et al. |
| 6,325,508 B1 | 12/2001 | Decreton et al. |
| 6,338,559 B1 | 1/2002 | Williams et al. |
| 6,350,031 B1 | 2/2002 | Lashkari et al. |
| 6,390,623 B1 | 5/2002 | Kokonaski et al. |
| 6,396,622 B1 | 5/2002 | Alden |
| 6,437,762 B1 | 8/2002 | Birdwell |
| 6,437,925 B1 | 8/2002 | Nishioka |
| 6,464,363 B1 | 10/2002 | Nishioka et al. |
| 6,491,391 B1 | 12/2002 | Blum et al. |
| 6,491,394 B1 | 12/2002 | Blum et al. |
| 6,501,443 B1 | 12/2002 | Mcmahon |
| 6,517,203 B1 | 2/2003 | Blum et al. |
| 6,554,425 B1 | 4/2003 | Roffman et al. |
| 6,609,794 B2 | 8/2003 | Levine |
| 6,614,408 B1 | 9/2003 | Mann |
| 6,616,275 B1 | 9/2003 | Dick et al. |
| 6,616,279 B1 | 9/2003 | Davis et al. |
| 6,618,208 B1 | 9/2003 | Silver |
| 6,619,799 B1 | 9/2003 | Blum et al. |
| 6,626,532 B1 | 9/2003 | Nishioka et al. |
| 6,631,001 B2 | 10/2003 | Kuiseko |
| 6,638,304 B2 | 10/2003 | Azar |
| 6,643,552 B2 | 11/2003 | Edell et al. |
| 6,652,096 B1 | 11/2003 | Morris et al. |
| 6,667,471 B2 | 12/2003 | Bos et al. |
| 6,682,195 B2 | 1/2004 | Dreher |
| 6,705,729 B2 | 3/2004 | Piers et al. |
| 6,709,105 B2 | 3/2004 | Menezes |
| 6,709,107 B2 | 3/2004 | Jiang et al. |
| 6,709,108 B2 | 3/2004 | Levine et al. |
| 6,714,133 B2 | 3/2004 | Hum et al. |
| 6,733,130 B2 | 5/2004 | Blum et al. |
| 6,738,199 B2 | 5/2004 | Nishioka |
| 6,768,536 B2 | 7/2004 | Okuwaki et al. |
| 6,769,767 B2 | 8/2004 | Swab et al. |
| 6,774,871 B2 | 8/2004 | Birdwell |
| 6,778,246 B2 | 8/2004 | Sun et al. |
| 6,793,340 B1 | 9/2004 | Morris et al. |
| 6,830,193 B2 | 12/2004 | Tanaka |
| 6,833,938 B2 | 12/2004 | Nishioka |
| 6,840,619 B2 | 1/2005 | Dreher |
| 6,851,805 B2 | 2/2005 | Blum et al. |
| 6,857,741 B2 | 2/2005 | Blum et al. |
| 6,859,333 B1 | 2/2005 | Ren et al. |
| 6,871,951 B2 | 3/2005 | Blum et al. |
| 6,883,916 B2 | 4/2005 | Menezes |
| 6,886,938 B1 | 5/2005 | Menezes |
| 6,893,124 B1 | 5/2005 | Kurtin |
| 6,894,751 B2 | 5/2005 | Payne et al. |
| 6,902,271 B2 | 6/2005 | Perrott et al. |
| 6,918,570 B2 | 7/2005 | Ahn |
| 6,918,670 B2 | 7/2005 | Blum et al. |
| 6,948,818 B2 | 9/2005 | Williams et al. |
| 6,951,391 B2 | 10/2005 | Michael et al. |
| 6,955,433 B1 | 10/2005 | Benjamin et al. |
| 6,956,682 B2 | 10/2005 | Benjamin |
| 6,976,982 B2 | 12/2005 | Santini et al. |
| 6,986,579 B2 | 1/2006 | Blum et al. |
| 7,008,054 B1 | 3/2006 | Kurtin et al. |
| 7,009,757 B2 | 3/2006 | Nishioka et al. |
| 7,018,040 B2 | 3/2006 | Blum et al. |
| 7,019,890 B2 | 3/2006 | Meredith et al. |
| 7,023,594 B2 | 4/2006 | Blum et al. |
| 7,034,619 B2 | 4/2006 | Lynch |
| 7,041,133 B1 | 5/2006 | Azar |
| 7,077,519 B2 | 7/2006 | Blum et al. |
| 7,085,065 B2 | 8/2006 | Silver |
| 7,130,664 B1 | 10/2006 | Williams |
| 7,133,172 B2 | 11/2006 | Nishioka |
| 7,137,702 B2 | 11/2006 | Piers et al. |
| 7,159,981 B2 | 1/2007 | Kato |
| 7,159,983 B2 | 1/2007 | Menezes et al. |
| 7,188,948 B2 | 3/2007 | Blum et al. |
| 7,192,136 B2 | 3/2007 | Howell et al. |
| 7,195,353 B2 | 3/2007 | Blum et al. |
| 7,209,097 B2 | 4/2007 | Suyama et al. |
| 7,229,173 B2 | 6/2007 | Menezes |
| 7,255,437 B2 | 8/2007 | Howell et al. |
| 7,290,876 B2 | 11/2007 | Duston et al. |
| 7,380,936 B2 | 6/2008 | Howell et al. |
| 7,396,126 B2 | 7/2008 | Blum et al. |
| 7,401,918 B2 | 7/2008 | Howell et al. |
| 7,404,636 B2 | 7/2008 | Blum et al. |
| 7,438,410 B1 | 10/2008 | Howell et al. |
| 7,461,936 B2 | 12/2008 | Jannard |
| 7,475,984 B2 | 1/2009 | Blum et al. |
| 7,481,531 B2 | 1/2009 | Howell et al. |
| 7,500,746 B1 | 3/2009 | Howell et al. |
| 7,500,747 B2 | 3/2009 | Howell et al. |
| 7,543,934 B2 | 6/2009 | Howell et al. |
| 7,581,833 B2 | 9/2009 | Howell et al. |
| 7,607,775 B2 | 10/2009 | Hermanson et al. |
| 7,621,634 B2 | 11/2009 | Howell et al. |
| 7,631,968 B1 * | 12/2009 | Dobson ............... H04M 1/05 351/158 |
| 7,677,723 B2 | 3/2010 | Howell et al. |
| 7,760,898 B2 | 7/2010 | Howell et al. |

(56) References Cited

U.S. PATENT DOCUMENTS

| | | |
|---|---|---|
| 7,771,046 B2 | 8/2010 | Howell et al. |
| 7,792,552 B2 | 9/2010 | D et al. |
| 7,806,525 B2 | 10/2010 | Howell et al. |
| 7,831,055 B2 | 11/2010 | Frerking et al. |
| 7,922,321 B2 | 4/2011 | Howell et al. |
| 7,988,283 B2 | 8/2011 | Jannard |
| 8,025,396 B1 | 9/2011 | Power |
| 8,089,511 B2 | 1/2012 | Yamamoto |
| 8,109,629 B2 | 2/2012 | Howell et al. |
| 8,174,569 B2 | 5/2012 | Tanijiri et al. |
| 8,337,013 B2 | 12/2012 | Howell et al. |
| 8,430,507 B2 | 4/2013 | Howell et al. |
| 8,434,863 B2 | 5/2013 | Howell et al. |
| 8,465,151 B2 | 6/2013 | Howell et al. |
| 8,500,271 B2 | 8/2013 | Howell et al. |
| 8,770,742 B2 | 7/2014 | Howell et al. |
| 8,915,588 B2 | 12/2014 | Blum et al. |
| 8,931,896 B2 | 1/2015 | Blum et al. |
| 9,122,083 B2 | 9/2015 | Blum et al. |
| 9,124,796 B2 | 9/2015 | Blum et al. |
| 10,114,235 B2 | 10/2018 | Blum et al. |
| 10,598,960 B2 * | 3/2020 | Blum .................. G02C 11/10 |
| 2001/0055094 A1 | 12/2001 | Zhang |
| 2002/0049374 A1 | 4/2002 | Abreu |
| 2002/0060525 A1 | 5/2002 | Sagano et al. |
| 2002/0140899 A1 | 10/2002 | Blum et al. |
| 2002/0149739 A1 | 10/2002 | Perrott et al. |
| 2002/0186346 A1 | 12/2002 | Stantz et al. |
| 2003/0018383 A1 | 1/2003 | Azar |
| 2003/0103413 A1 | 6/2003 | Jacobi et al. |
| 2003/0112523 A1 | 6/2003 | Daniell |
| 2003/0151721 A1 | 8/2003 | Lai et al. |
| 2003/0199978 A1 | 10/2003 | Lindsey et al. |
| 2003/0208265 A1 | 11/2003 | Ho et al. |
| 2003/0210377 A1 | 11/2003 | Blum et al. |
| 2004/0000733 A1 | 1/2004 | Swab et al. |
| 2004/0008157 A1 | 1/2004 | Brubaker et al. |
| 2004/0008319 A1 | 1/2004 | Lai et al. |
| 2004/0108971 A1 | 6/2004 | Waldern et al. |
| 2004/0117011 A1 | 6/2004 | Aharon et al. |
| 2004/0130677 A1 | 7/2004 | Liang et al. |
| 2004/0160573 A1 | 8/2004 | Jannard et al. |
| 2004/0179280 A1 | 9/2004 | Nishioka |
| 2004/0181404 A1 * | 9/2004 | Shedd .................. G02B 30/34 704/235 |
| 2004/0186533 A1 | 9/2004 | Greenberg et al. |
| 2004/0196435 A1 | 10/2004 | Dick et al. |
| 2004/0235416 A1 * | 11/2004 | Chan .................. H04H 20/28 455/3.04 |
| 2004/0239874 A1 | 12/2004 | Swab et al. |
| 2004/0246440 A1 | 12/2004 | Andino et al. |
| 2005/0049578 A1 | 3/2005 | Tu et al. |
| 2005/0073739 A1 | 4/2005 | Meredith et al. |
| 2005/0078274 A1 | 4/2005 | Howell et al. |
| 2005/0099594 A1 | 5/2005 | Blum et al. |
| 2005/0113912 A1 | 5/2005 | Feenstra et al. |
| 2005/0124983 A1 | 6/2005 | Frey et al. |
| 2005/0237485 A1 | 10/2005 | Blum et al. |
| 2006/0044510 A1 | 3/2006 | Williams et al. |
| 2006/0066808 A1 | 3/2006 | Blum et al. |
| 2006/0095128 A1 | 5/2006 | Blum et al. |
| 2006/0113054 A1 | 6/2006 | Silvestrini |
| 2006/0122531 A1 | 6/2006 | Goodall et al. |
| 2006/0132382 A1 * | 6/2006 | Jannard .................. G02C 11/06 345/8 |
| 2006/0154642 A1 * | 7/2006 | Scannell, Jr. .......... G08B 7/066 455/404.1 |
| 2006/0164593 A1 | 7/2006 | Peyghambarian et al. |
| 2006/0173367 A1 | 8/2006 | Stuart et al. |
| 2006/0177086 A1 | 8/2006 | Rye et al. |
| 2006/0183986 A1 | 8/2006 | Rice et al. |
| 2007/0030442 A1 | 2/2007 | Howell et al. |
| 2008/0001735 A1 * | 1/2008 | Tran .................. A61B 5/0077 340/539.22 |
| 2008/0143954 A1 | 6/2008 | Abreu et al. |
| 2008/0218684 A1 | 9/2008 | Howell et al. |
| 2009/0251409 A1 * | 10/2009 | Parkinson .......... G02B 27/017 370/401 |
| 2009/0256977 A1 | 10/2009 | Haddock et al. |
| 2009/0296044 A1 | 12/2009 | Howell et al. |
| 2010/0045928 A1 * | 2/2010 | Levy .................. G02C 11/10 351/158 |
| 2010/0103076 A1 | 4/2010 | Yamamoto |
| 2010/0177277 A1 | 7/2010 | Kokonaski et al. |
| 2010/0292599 A1 | 11/2010 | Oleson et al. |
| 2011/0065428 A1 * | 3/2011 | Schroeter .......... H04M 1/72448 455/418 |
| 2011/0071459 A1 | 3/2011 | Rickard et al. |
| 2011/0249230 A1 | 10/2011 | Blum |
| 2013/0215374 A1 | 8/2013 | Blum et al. |
| 2013/0235332 A1 | 9/2013 | Blum et al. |
| 2013/0242253 A1 | 9/2013 | Blum et al. |
| 2013/0250135 A1 | 9/2013 | Blum et al. |
| 2014/0002753 A1 | 1/2014 | Griffin |
| 2015/0335420 A1 | 11/2015 | Blum et al. |
| 2018/0329234 A1 * | 11/2018 | Blum .................. G02C 11/06 |

FOREIGN PATENT DOCUMENTS

| | | |
|---|---|---|
| CN | 201222131 Y | 4/2009 |
| CN | 201464741 U | 5/2010 |
| DE | 4223395 A1 | 1/1994 |
| EP | 0154962 A2 | 9/1985 |
| EP | 0233104 A1 | 8/1987 |
| EP | 0237365 A1 | 9/1987 |
| EP | 0578833 A1 | 1/1994 |
| EP | 0649044 A1 | 4/1995 |
| EP | 0918248 A2 | 5/1999 |
| GB | 2169417 A | 7/1986 |
| GB | 2170613 A | 8/1986 |
| JP | S5576323 A | 6/1980 |
| JP | S58113912 A | 7/1983 |
| JP | S61156227 A | 7/1986 |
| JP | S61502221 A | 10/1986 |
| JP | S6357044 A | 3/1988 |
| JP | H01237610 A | 9/1989 |
| JP | H0423579 A | 1/1992 |
| JP | H0461495 A | 2/1992 |
| JP | H05100201 A | 4/1993 |
| JP | H0728002 A | 1/1995 |
| JP | H08508826 A | 9/1996 |
| JP | H11352445 A | 12/1999 |
| JP | 2001522063 A | 11/2001 |
| JP | 2002525769 A | 8/2002 |
| JP | 2002533158 A | 10/2002 |
| JP | 2003230590 A | 8/2003 |
| JP | 2003244776 A | 8/2003 |
| JP | 2003312391 A | 11/2003 |
| JP | 2005502902 A | 1/2005 |
| JP | 2000138858 A | 9/2007 |
| JP | 2007323062 A | 12/2007 |
| JP | 2008545287 A | 12/2008 |
| JP | 2011229024 A | 11/2011 |
| TW | 89113088 | 7/2008 |
| WO | 8505466 A1 | 12/1985 |
| WO | 9423334 A1 | 10/1994 |
| WO | 9923524 A1 | 5/1999 |
| WO | 0038593 A1 | 7/2000 |
| WO | 0106298 A1 | 1/2001 |
| WO | 03007851 A1 | 1/2003 |
| WO | 03050472 A1 | 6/2003 |
| WO | 03068059 A2 | 8/2003 |
| WO | 2004008189 A1 | 1/2004 |
| WO | 2004015460 A2 | 2/2004 |
| WO | 2004015481 A1 | 2/2004 |
| WO | 2004034095 A2 | 4/2004 |
| WO | 2004072687 A2 | 8/2004 |
| WO | 2006120416 A1 | 11/2006 |
| WO | 2010080999 A1 | 7/2010 |

(56) References Cited

OTHER PUBLICATIONS

Supplementary European Search Report of Application No. EP 05824718 dated Nov. 19, 2007.
Tarascon et al., "Issues and challenges facing rechargeable lithium batteries" Nature 2001, 414:359-367 (Nov. 15, 2001).
Thibos, Larry N., et al. "Use of Liquid-Crystal Adaptive-Optice to Alter the Refractive State of the Eye; Optometry and Vision Science" 74:7; American Academy of Optometry (Jul. 1997).
Thibos, Larry N., et al. "Vision through a liquid-crystal spatial light modulator" Adaptive Optics Conference; Durham, UK (1999).
Thibos, Larry, N., et al. "Electronic Spectacles for the 21 Century" Indian Journal of Optometry, 2:1 (Spring 1999).
U.S. Appl. No. 60/623,946, filed Nov. 2, 2004.
U.S. Appl. No. 60/623,947, filed Nov. 2, 2004.
U.S. Appl. No. 60/636,490, filed Dec. 17, 2004.
U.S. Appl. No. 60/661,925, filed Mar. 16, 2005.
U.S. Appl. No. 60/666,167, filed Mar. 30, 2005.
U.S. Appl. No. 60/667,094, filed Apr. 1, 2005.
U.S. Appl. No. 60/669,403, filed Apr. 8, 2005.
U.S. Appl. No. 60/673,758, filed Apr. 22, 2005.
U.S. Appl. No. 60/674,702, filed Apr. 26, 2005.
U.S. Appl. No. 60/679,241, filed May 10, 2005.
U.S. Appl. No. 60/685,407, filed May 31, 2005.
U.S. Appl. No. 60/687,341, filed Jun. 6, 2005.
U.S. Appl. No. 60/687,342, filed Jun. 6, 2005.
U.S. Appl. No. 60/692,270, filed Jul. 21, 2005.
Walter, P. et al., "Development of a completely encapsulated intraocular pressure sensor", Ophthalmic Research (2000); 32: 278-284.
Written Opinion in PCT/US2013/020571, dated Jul. 5, 2013, 6 pages.
Anderson, M. "Adaptive Optics: Liquid Crystals Lower the Cost of Adaptive Optics" Laser Focus World (Dec. 1999).
Bertsch, A. et al., "The Sensing Contact Lens", Medical Device Technology (2006); 17: 19-21.
Bradley, Arthur "Profile: Larry N. Thibos, PhD., and Donald T. Miller, PhD." Indian Journal of Optometry; 2:1 (Spring 1999).
Corrected Notice of Allowance in U.S. Appl. No. 13/735,887, dated Jul. 10, 2015, 2 pages.
Davis, Robert A. "Computer Vision Syndrome—The Eyestrain Epidemic" Review of Optometry (Sep. 15, 1997).
Donald T. Miller, Xin Hong, and Larry N. Thibos, "Requirements for the segmented spatial light modulators for diffraction-limited imaging through aberrated eyes," G.D. Love, ed. Proceedings of the 2nd International Workshop on Adaptive Optics for Industry and Medicine, World Scientific, Singapore, 63-68 (Jul. 1999).
Eggers, T. et al., "Wireless Intra-ocular Pressure Monitoring System Integrated in an Artificial Lens", Presented at the First Annual International IEEE-EMBS Special Topic Conference on Microtechnologies in Medicine & Biology, Lyon, France, Oct. 12-14, 2000; Paper 7: 466-469.
Eyecare Business (Oct. 1997).
Final Office Action dated Dec. 12, 2017 from U.S. Appl. No. 15/437,746, 13 pages.
Final Office Action dated Dec. 12, 2017 from U.S. Appl. No. 15/438,104, 12 pages.
Final Office Action dated Oct. 10, 2017 from U.S. Appl. No. 15/440,675, 17 pages.
International Preliminary Report on Patentability in PCT/US05/39101, dated May 8, 2007, 4 pages.
International Preliminary Report on Patentability in PCT/US2013/020571, dated Jul. 8, 2014, 7 pages.
International Search Report corresponding to the PCT/US09/037544 application dated May 20, 2009.
International Search Report for Application No. PCT/US 08/54721 dated Aug. 20, 2008.
International Search Report in PCT/US2013/020571, dated Jul. 5, 2013, 4 pages.
International Search Report of Application No. PCT/US05/39101 dated Jul. 7, 2006.

International Search Report of Application No. PCT/US08/51649 dated Jul. 7, 2008.
Kowel, Stephen T., et al "Focusing by electrical modulation of refraction in a liquid crystal cell" Applied Optics23:2 (Jan. 15, 1984).
Lazarus, Stuart M. "The Use of Yoked Base-Up and Base-In Prism for Reducing Eye Strain at the Computer" Journal of the American Optometric Association (Apr. 1996).
Leonardi, M. et al., "A Soft Contact Lens with a MEMS Strain Gage Embedded for Intraocular Pressure Monitoring", Transducers '03; The 12th International Conference on Solid Slate Sensors, Actuators and Microsyslems, Boston, Jun. 8-12, 2003; 3B2.5: 1043-1046.
Leonardi, M. et al., "First Steps toward Noninvasive IOP—Monitoring with a Sensing Contact Lens", Investigative Ophthalmology & Visual Science (2004); 45(9): 3113-3117.
Naumov, A.F. "Control Optimization of Spherical Modal Liquid Crystal Lenses", Optics Express 4:9; Optical Society of America (Apr. 26, 1999).
Naumov, A.F. "Liquid Crystal Adaptive Lenses with Modal Control" Optics Letters, 23:13 Optical Society of America (Jul. 1, 1998).
Non-Final Office Action dated Aug. 10, 2017 from U.S. Appl. No. 15/613,733, 19 pages.
Non-Final Office Action dated Dec. 1, 2017 from U.S. Appl. No. 14/816,249, 12 pages.
Non-Final Office Action dated Jun. 14, 2017 from U.S. Appl. No. 15/440,675, 18 pages.
Non-Final Office Action dated Jun. 30, 2017 from U.S. Appl. No. 15/437,746, 12 pages.
Non-Final Office Action dated Jun. 30, 2017 from U.S. Appl. No. 15/438,104, 10 pages.
Notice of Allowance dated May 24, 2017 from U.S. Appl. No. 14/816,249, 8 pages.
Notice of Allowance in U.S. Appl. No. 13/735,887, dated Apr. 28, 2015, 8 pages.
Notice of Allowance in U.S. Appl. No. 13/779,232, dated Sep. 18, 2014, 10 pages.
Notice of Allowance in U.S. Appl. No. 13/779,320, dated Apr. 28, 2015, 8 pages.
Notice of Allowance in U.S. Appl. No. 13/779,407, dated Jun. 26, 2014, 8 pages.
Notice of Allowance in U.S. Appl. No. 13/779,407, dated Sep. 15, 2014, 5 pages.
Office Action (Ex Parte Quayle Action) issued in corresponding U.S. Appl. No. 13/779,320 dated Mar. 17, 2014, 7 pages.
Office Action (Ex-Parte Quayle Action) in U.S. Appl. No. 13/779,232, dated May 16, 2014, 5 pages.
Office Action and Search Report in CN Application No. 201310009498.3, dated Apr. 29, 2015 (and English translation), 36 pages.
Office Action in CN Application No. 201380009013.9, dated May 26, 2015 (and English translation), 36 pages.
Office Action in corresponding U.S. Appl. No. 13/779,232, dated Dec. 24, 2013, 9 pages.
Office Action in corresponding U.S. Appl. No. 13/779,407 dated Mar. 17, 2014, 6 pages.
Office Action in corresponding U.S. Appl. No. 13/779,407, dated Sep. 17, 2013, 10 pages.
Office Action in U.S. Appl. No. 13/779,320, dated Feb. 6, 2015, 7 pages.
Office Action in U.S. Appl. No. 14/816,249, dated Dec. 20, 2016, 7 pages.
Office Action in U.S. Appl. No. 15/438,104, dated Apr. 19, 2017, 8 pages.
Office Action issued in corresponding U.S. Appl. No. 13/779,320 dated Sep. 17, 2013, 13 pages.
Optics, Org, Dec. 19, 2006 "Liquid Lenses Eye Commercial Breakthrough" Opto & Laser Europe (Nov. 2003).
Pitchon, E.M. et al., "First In-Vivo Human Monitoring of Intraocular Pressure Fluctuation and Ocular Pulsation by a Wireless Soft Contact Lens Sensor." Congress of the European Glaucoma Society, Berlin, Jun. 2008; Congres annuel de la Societe francaise d'ophtalmologie, Paris, May 2008; ARVO Meeting (The Association for Research in Vision and Ophthalmology), Apr. 27-May 1,

(56) References Cited

OTHER PUBLICATIONS

2008, Fort Lauderdale American Glaucoma Society, 18th Annual Meeting, Mar. 2008, Washington, 1 page.
Restriction Requirement in U.S. Appl. No. 13/779,320, dated Jul. 17, 2014, 8 pages.
Search Report and Written Opinion in PCT/US05/39101, dated Jul. 7, 2006, 5 pages.

* cited by examiner

EYEWEAR DOCKING STATION AND ELECTRONIC MODULE

CROSS-REFERENCE TO RELATED APPLICATIONS

The present application is a continuation of U.S. application Ser. No. 15/975,353, filed on May 9, 2018, which is a continuation of U.S. application Ser. No. 14/808,239, now U.S. Pat. No. 10,114,235, filed on Jul. 24, 2015, which is a continuation of U.S. application Ser. No. 13/735,887, now U.S. Pat. No. 9,122,083, which was filed on Jan. 7, 2013, and which claims priority to each of the following provisional patent applications: U.S. Application No. 61/583,940, filed on Jan. 6, 2012; U.S. Application No. 61/622,092, filed on Apr. 10, 2012; U.S. Application No. 61/638,150, filed on Apr. 25, 2012; and U.S. Application No. 61/640,425, filed on Apr. 30, 2012, the contents of each of which are incorporated herein by reference in their entireties. U.S. application Ser. No. 11/261,035, filed on Oct. 28, 2005, now U.S. Pat. No. 8,778,022, is also incorporated herein by reference in its entirety.

BACKGROUND

Presently, commercial eyewear comprising electronics are limited to one application in addition to the conventional eyeglass lenses housed within said eyewear. By way of example only, there are commercially available electronic focusing eyeglasses, commercially available eyeglasses with a built in MP3 player, commercially available eyeglasses with video for occupation purposes, and soon there are expected to be commercially available eyeglasses with a built in camera. However, with the exception of inventor's patent application Ser. No. 13/085,562, the prior art teaches eyeglasses capable of one or more applications, but in all cases the applications are built into the eyeglasses or, if attached to the eyeglass frames, do so such that only one application device at a time is available in addition to the standard lenses housed by the eyeglass frames. Inventor's prior patent application Ser. No. 13/085,562 teaches the front of eyewear being used as a docking station for applying a clip on means which can house various application devices. The application devices receive at least some of their electrical power needed to drive the application devices. While patent application Ser. No. 13/085,562 teaches a means of applying (one at a time) a plurality of application devices to eyewear the means of doing so causes the lenses to look thick, adds weight to the front of the eyewear, and distracts from the aesthetics of the eyewear.

Today there are so many electronic devices each capable of providing an occupational benefit or personal benefit for the user. These electronic devices have been in many cases miniaturized. The modern world operates at a very high pace whereby being able to provide benefits to the user in a hands free manner is very efficient and beneficial. However, if one wants to purchase "fashionable" eyewear capable of being used for a plurality of functions beyond correcting the refractive error of the wearer and/or providing a tinted means to make the wearer's eyes more comfortable, such eyewear does not exist. Needless to say there is a need for a single pair of fashionable eyewear capable of a utilizing one or more of a multitude of different application devices while the wearer is wearing the eyewear.

SUMMARY

The present subject matter is directed to electronic eyewear modules and systems to be worn by a wearer, whereby an electronic eyewear system with a docking station can be easily joined with a plurality of electronic application modules (also referred to herein as application devices or application modules), preferably in a standardized manner. These application modules can each fit together with the docking station and may be utilized one or more at a time while the eyewear is being worn by a wearer. The modularity may also provide a user with a variety of interchangeable applications, each of which may be recognized by the eyewear system. In the event that electronic application modules break, they can also be easily replaced without replacing the entire system.

The invention disclosed herein allows for the eyewear to remain fashionable and does not distract from the cosmetic design of the eyewear. Furthermore the invention disclosed herein provides additional weight of one or more application devices to be distributed in a comfortable manner when worn by the wearer.

According to first aspects of the invention, an application module is provided that is adapted to be mounted to an eyewear docking station. The application module may include one or more of an electronic device configured to perform a function; an attachment mechanism configured to secure the application module to the docking station in a substantially fixed position; and/or a plurality of preconfigured application connection points. In embodiments, the plurality of preconfigured application connection points may include at least two different sub-function connections used to support the function of the electronic device.

In embodiments, the application connection points may be configured to attach to a universal connector cable. In embodiments, the application connection points may be configured to connect directly to corresponding application connection points of an eyewear frame.

In embodiments, the different sub-function connections may include at least two of power supply, audio out, audio in, audio ground, video out, and video in. In embodiments, the different sub-function connections may further include data output, data input, control signal output, and/or control signal input.

In embodiments, the different sub-function connections may preferably include a power supply, an audio out, and control input.

In embodiments, the different sub-function connections may preferably include a data input and a control signal output. In embodiments, the data input may include sensor data, and the application module may be configured to control a lens function of the eyewear via the control signal output based on the data input.

In embodiments, the different sub-function connections may preferably include a power supply configured for the application module to receive at least one of operating power and recharging power from the eyewear.

In embodiments, the function of the electronic device may include at least one of audio playback, audio recording, acoustic amplification, acoustic canceling, hearing aid, video playback, video recording, photography, fall detection, alertness monitoring, pedometer, geo-location, pulse detector, wireless communication (e.g. cellular phone, Bluetooth, WiFi, IR, etc.), virtual reality, augmented reality, gaming, eye tracking, pupil monitoring, lens control, automated reminder, visible and/or non-visible lighting, lasing, IR and/or thermal detection, and alarm, any of which may be provided to a user via the eyewear.

In embodiments, the electronic device is configured to provide at least one of virtual reality and augmented reality to a user via the eyewear.

In embodiments, each application module may include its own circuitry and logic sufficient to control the function of the application module, and/or to control function of a device included within the eyewear frame.

In embodiments, the attachment mechanism may include one or more of pins, detents, rails, magnets, sockets, or other means known in the art for joining small components together, preferably in a releasable manner.

In embodiments, the application module may be configured to provide a recognizable signal, and/or may include a recognizable feature, such that the eyewear can determine the function of the application module, a type of the application module, and/or variable capabilities of the application module.

In embodiments, the application module may be substantially water resistant, sweat resistant, water proof, and/or wear resistant.

According to further aspects of the invention, an eyewear system may be provided including an eyewear frame with a docking station, and an application module adapted to be mounted to the docking station. In embodiments, the eyewear frame may include an electronic connector including a first set of preconfigured application connection points, and the application module may include an electronic device configured to perform a function and a second set of preconfigured application connection points corresponding to at least some of the first set of preconfigured application connection points. In embodiments, the second set of preconfigured application connection points may include at least two different sub-function connections used to support the function of the electronic device.

In embodiments, the application connection points may be configured to attach to a universal connector cable. In embodiments, the eyewear system may further include the universal connector cable. In embodiments, the eyewear frame may be configured to connect to the universal connector cable, and for connecting the application connection points to the universal connector cable.

In embodiments, the application connection points of the application module may be configured to connect directly to corresponding application connection points of the eyewear frame.

In embodiments, the different sub-function connections may include at least two of power supply, audio out, audio in, audio ground, video out, and video in. In embodiments, the different sub-function connections may further include data output, data input, control signal output, and/or control signal input.

In embodiments, the different sub-function connections may preferably include a power supply configured for the application module to receive at least one of operating power and recharging power from the eyewear frame.

In embodiments, the function of the electronic device may include at least one of audio playback, audio recording, acoustic amplification, acoustic canceling, hearing aid, video playback, video recording, photography, fall detection, alertness monitoring, pedometer, geo-location, pulse detector, wireless communication, virtual reality, augmented reality, gaming, eye tracking, pupil monitoring, lens control, automated reminder, lighting, lasing, and alarm.

In embodiments, the eyewear frame may include a lens, and the electronic device may be configured to at least partially control said lens. For example, the lens may be an electro-active lens and the electronic device may be configured to control a focus, tint or other change of the lens based on sensed conditions (such as lighting) and/or user commands. In other embodiments, the lens may have built in display functions that can be controlled by the electronic device, such as with virtual or augmented reality, or gaming.

In embodiments, the eyewear lens may be one of a dynamic focusing lens, static focusing lens, tinted lens, photochromic lens, electrochromic lens, thermochromic lens, or display.

In embodiments, the eyewear frame may include a speaker, and the electronic device may be configured to provide an audio signal to the speaker.

In embodiments where the eyewear frame includes at least one of a speaker and a lens, the electronic device may be configured to provide at least one of virtual reality and augmented reality to a user via the speaker and/or lens.

In embodiments, the eyewear frame may include one or more of removable or fixed storage media, a communication device, a power source, a microphone, a bone-phone, a microprocessor, In embodiments wherein the eyewear frame includes a power source, the power source may be, for example, a rechargeable battery, disposable battery, fuel cell, solar cell, or kinetic energy source.

In embodiments, the eyewear frame may be configured to determine one or more of the function of the application module, a type of the application module, and/or variable capabilities of the application module based on a recognizable signal from, or other characteristic of, the application module.

In embodiments, the docking station and/or application module may be configured to convert the application module from a non-functioning application module into that of a functioning application module upon being docked to said docking station.

According to further aspects of the invention, an electronic eyewear system to be worn by a wearer is provided, whereby said electronic eyewear system comprises a means of securing said eyewear to the head of a wearer, an eyewear front, a docking station which is part of said eyewear, a plurality of application device modules which each can fit into said docking station one at a time and whereby the docking station provides for enabling the routing of electrical power to the application device module.

In embodiments, the application device modules devices may be utilized more than one at a time while the eyewear is being worn by a wearer.

Embodiments may further include a controller configured to be connected to the application device modules.

Embodiments may further include a multi-function connector configured to connect to the application device modules, and to provide at least two functions to the application device modules via said controller.

In embodiments, the application device modules may include at least one camera and at least one microphone.

In embodiments, the application device modules may include at least two cameras configured to be mounted for stereoscopic imaging.

In embodiments, the application device modules may include at least two hearing aids configured to be mounted in proximity to opposite ears of the wearer.

The application device modules may include one or more of still photo camera, video camera, digital audio player, display, projector, hearing aid, fall detector, alertness monitor, pedometer, pulse detector, cell phone, audio system, communication system, video system, music system, audio system, $CO_2$ detector, poor air quality alert device, bad breath detector, thermometer, refractive error measurement device, GPS system, virtual reality system, augmented reality system, gaming system, eye tracking device, pupil monitor device, sensor, smoke detector, pill reminder, medication reminder, speaker, light, laser.

In some embodiments, the eyewear system can include an intermediate electrical contact. A functional member of the eyewear (e.g. active lens, speaker, sensor, microprocessor, or other device located in the eyewear frame) can include an electrical connector, and the intermediate electrical contact can connect the electronics of the application module to the functional member. The intermediate electrical contact can be a plug-and-receptacle electrical contact. In some embodiments, the intermediate electrical contact is located at one of: a rim of the eyewear, the rear ⅓ of the temple, the middle of the temple, the forward ⅓ of the temple, the rim lock or hinge, of the eyewear, a surface of the optical functional member, a frame front of the eyewear, an electronic display, an electronic controller, and between the rim and the lens of the eyewear.

In some embodiments, the eyewear frame can include a temple and a rimlock. In those embodiments, the functional member of the eyewear can be located in the temple, and a connective element can be routed from the application module through the rimlock to the optical functional member. In some embodiments, the rimlock includes an upper rimlock and a lower rimlock, and the connective element is routed between the upper rimlock and the lower rimlock. The rimlock can include upper rimlock and a lower rimlock, and the connective element can form a layer between the upper rimlock and the lower rimlock. The layer can be insulating. In some embodiments, the connective element can be a conductive compressible member that can be conductive rubber. In some embodiments, the connective element comprises a multi-conductor cable.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention claimed. The detailed description and the specific examples, however, indicate only preferred embodiments of the invention. Various changes and modifications within the spirit and scope of the invention will become apparent to those skilled in the art from this detailed description.

DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced. In the drawings.

DETAILED DESCRIPTION

Figure 1:
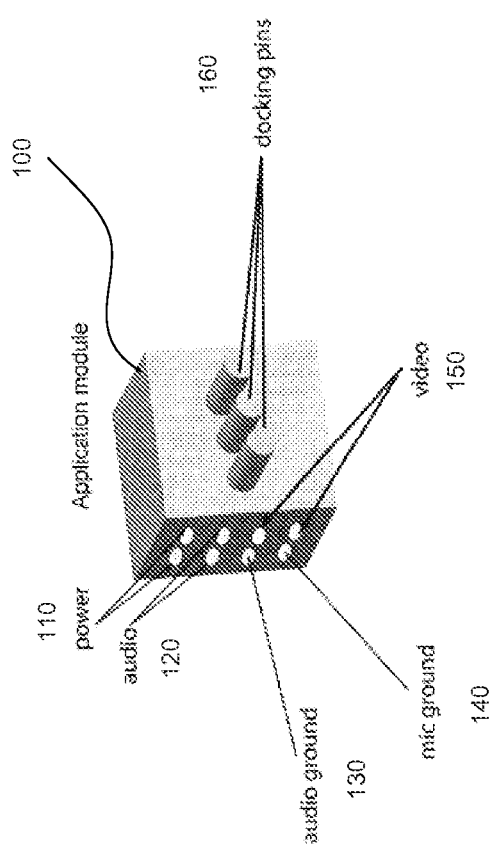
FIG. 1 illustrates an exemplary application module in accordance with an aspect of the present invention.

It is understood that the invention is not limited to the particular methodology, protocols, etc., described herein, as these may vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a," "an," and "the" include the plural reference unless the context clearly dictates otherwise. Thus, for example, a reference to "a module" is a reference to one or more modules and equivalents thereof known to those skilled in the art.

Unless defined otherwise, all technical terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Some terms that are used herein are described in further detail as follows:

As used herein, the term "approximately" may refer to plus or minus 10 percent, inclusive. Thus, the phrase "approximately 10 mm" may be understood to mean from 9 mm to 11 mm, inclusive. As used herein, the term "substantially" may refer to plus or minus a percent that is recognized as within manufacturing tolerances or other unintended or inconsequential variations.

As used herein, the term "comprising" is not intended to be limiting, but may be a transitional term synonymous with "including," "containing," or "characterized by." The term "comprising" may thereby be inclusive or open-ended and does not exclude additional, unrecited elements or method steps when used in a claim or to describe an embodiment. For instance, in describing a method, "comprising" indicates that the claim is open-ended and allows for additional steps. In describing a device, "comprising" may mean that a named element(s) may be essential for an embodiment, but other elements may be added and still form a construct within the scope of a claim. In contrast, the transitional phrase "consisting of excludes any element, step, or ingredient not specified in a claim. This is consistent with the use of the term throughout the specification.

As used herein, a "conductive path" refers to a continuous path for which electrons (i.e. current) may flow from one point to another. The conductive path may comprise one component, or more than one component. For instance, a conductive path may comprise portions of a lens housing, a temple, a hinge, a lens, and/or conductive material disposed between (or within) some or all of the components.

As used herein, "coupled" may refer to any manner of connecting two components together in any suitable manner, such as by way of example only: attaching (e.g. attached to a surface), disposing on, disposing within, disposing substantially within, embedding within, embedded substantially within, etc. "Coupled" may further comprise fixedly attaching two components (such as by using a screw, an adhesive, or embedding a first component into a second component during a manufacturing process), but does not so require. Two components may be coupled temporarily simply by being in physical contact with one another. Two components are "electrically coupled" or "electrically connected" if current can flow from one component to another. That is, the two components do not have to be in direct contact such that current flows from the one component directly to the other component. There may be any number of other conductive materials and components disposed electrically between two components "electrically coupled" so long as current can flow there between.

As used herein, a "dynamic lens" may refer to a lens with an optical power which is alterable with the application of electrical energy, mechanical energy or force. Either the entire lens may have an alterable optical power, or only a portion, region or zone of the lens may have an alterable optical power. The optical power of such a lens is dynamic or tunable such that the optical power can be switched between two or more optical powers. The switching may comprise a discrete change from one optical power to another (such as going from an "off" or inactive state to an "on" or active state) or it may comprise continuous change from a first optical power to a second optical power, such as by varying the amount of electrical energy to a dynamic element (e.g. tunable). One of the optical powers may be that of substantially no optical power. A dynamic lens may also be referred to as a dynamic optic, a dynamic optical element, a dynamic optical zone, dynamic power zone, or a dynamic optical region.

As used herein, an "eyewear frame" is intended to generally refer to a complete wearable housing that secures at least one element in a location relative to the wearer's eyes when being worn such that the wearer can see, or see through, the element. The eyewear frame may comprise elements such as a first and second temple, a lens housing that is configured to support a lenses, one or more hinges, and any other related component. On the other hand, a "spectacle frame" may refer to a complete wearable housing that secures spectacle lenses and aligns them in the proper place relative to the wearer's eyes when being worn. The frame may comprise elements such as a first and second temple, a lens housing that is configured to support the spectacle lenses, one or more hinges, and any other related component.

As used herein, a "lens" may refer to any device or portion of a device that causes light to converge or diverge. The device may be static or dynamic. A lens may be refractive or diffractive. A lens may be concave, convex or plano on one or both surfaces. A lens may be spherical, cylindrical, prismatic or a combination thereof. A lens may be made of optical glass, plastic or resin. A lens may also be referred to as an optical element, an optical zone, an optical region, an optical power region or an optic. It should be noted that within the optical industry a lens can be referred to as a lens even if it has zero optical power. Moreover, a lens may refer to both intra-ocular and extra-ocular components.

As used herein, a "lens housing" may refer to a part of the frame that is configured or adapted to support or hold the first and the second lenses in place (preferably firmly in place). The lens housing may also comprise the part of the frame to which the temples attach. The lens housing may comprise any component or material adapted to support the lenses, including, for example, screws, nylon monofilament, eye-wire, etc. or any combination thereof. The lens housing may comprise any material, including metal or plastic. A lens housing may be included in any type of frame design, including fully rimmed, semi-rimless, and rimless. In some embodiments, the lens housing may also include the bridge, such as when the lens housing comprising a single component or two components that support both the first and the second lens.

As used herein, a "multi-focal lens" may refer to a lens having more than one focal point or optical power. Such lenses may be static or dynamic. Examples of static multi-focal lenses include a bifocal lens, trifocal lens or a Progressive Addition Lens. Examples of dynamic multifocal lenses include electro-active lenses whereby various optical powers may be created in the lens depending on the types of electrodes used, voltages applied to the electrodes and index of refraction altered within a thin layer of liquid crystal.

Multifocal lenses may also be a combination of static and dynamic. For example, an electro-active element may be used in optical communication with a static spherical lens, static single vision lens, and static multifocal lens such as, by way of example only, a Progressive Addition Lens.

As used herein, an "ophthalmic lens" may refer to a lens suitable for vision correction, which may include a spectacle lens, a contact lens, an intra-ocular lens, a corneal in-lay, and a corneal on-lay.

As used herein, a "substrate" is a component that is generally well-known in the field of optics. A substrate typically refers to the component of a lens that is first fabricated or provided, and on which additional layers or materials may be deposited. A substrate may have dimensions on the order of millimeters or fractions of millimeters, whereas coatings and other deposited layers on the substrate typically have dimensions (i.e. thicknesses) that are on the order of microns. Examples of substrates may include, for example, lens blanks, semi-finished lens-blanks, or lens wafers.

Turning to the figures, FIG. 1 illustrates an exemplary application module in accordance with an aspect of the present invention. In particular, application module 100 is adapted to be mounted to an eyewear docking station, examples of which are described further below. In the example shown in FIG. 1, the application module 100 includes docking pins 160 that are configured to plug into corresponding sockets in an eyewear frame (not shown). In embodiments, application module 100 may also be sized to fit within a recess in an eyewear frame, though it can also be attached external to the eyewear frame.

Application module 100 may include one or more electronic device(s) configured to perform one or more functions such as, for example, of audio playback, audio recording, acoustic amplification, acoustic canceling, hearing aid, video playback, video recording, photography, fall detection, alertness monitoring, pedometer, geo-location, pulse detector, wireless communication (e.g. cellular phone, Bluetooth, WiFi, IR, etc.), virtual reality, augmented reality, gaming, eye tracking, pupil monitoring, lens control, automated reminder, visible and/or non-visible lighting, lasing, IR and/or thermal detection, and alarm, any of which may be provided to a user via the eyewear. One advantage of the present subject matter is that, as discussed further below, a variety of functional modules may be interchanged with an eyewear system using a "universal docking station," which includes a plurality of standardized connection points, e.g. power, audio, video etc. In embodiments, the audio and/or video may be analog connections. Thus, the modules can be relatively small, lightweight, with reduced processing capability than might otherwise be required, e.g. if the connection only allowed for digital data transmission. In embodiments, the connections may further include data output, data input, control signal output, and/or control signal input. Each application module may include its own circuitry and logic sufficient to control the function of the application module, and/or to control function of a device included within the eyewear frame.

In preferred embodiments, the electronic device is configured to control an aspect of an electronic lens, and/or provide at least one of virtual reality and augmented reality to a user via the eyewear.

Returning to FIG. 1, it should be noted that the attachment mechanism including the fixed pins can take many forms, e.g. one or more of pins, detents, rails, magnets, sockets, or other means known in the art for joining small components together, preferably in a releasable manner. These can be configured to secure the application module to a docking station in a relatively fixed position.

As also shown in FIG. 1, the application module 100 includes a plurality of preconfigured application connection points, also referred to as sub-function connections, in this case power connections 110, audio connections 120, audio ground 130, microphone ground 140, and video 150. In embodiments, the different sub-function connections may include at least two of power supply, audio out, audio in, audio ground, video out, and video in. In embodiments, the different sub-function connections may further include data output, data input, control signal output, and/or control signal input.

The examples shown in FIG. 1 are merely exemplary, as a variety of such connection points are contemplated as within the scope of the invention. Indeed, it is expected that various application modules will use only a subset of the preconfigured application points which are supported by the eyewear frame. This is intended to, for example, improve with the ease of modularity related to the design. The actual preconfigured application connection points included in a particular application module may include different sub-function connections used to support the function of the electronic device. For example, if the device included in the module is intended to function as a hearing aid, it may typically include a power connection, an audio out connection, and an audio in connection, and may include one or more data/command connections to provide, for example, additional processing support or functionality. Some non-limiting, but preferable, examples of pre-configured sub-function connections may include a power supply, an audio out, and control input; a data input and a control signal output; a power supply configured for the application module to receive at least one of operating power and recharging power from the eyewear. In embodiments, the data input may include sensor data, and the application module may be configured to control a lens function of the eyewear via the control signal output based on the data input.

It should be appreciated that, as discussed further below, the application connection points may be configured to attach to a universal connector cable and/or to connect directly to corresponding application connection points of an eyewear frame.

The application module 100 may be configured to provide a recognizable signal, e.g. though a data, or other, connection point, and/or may include a recognizable feature (e.g. a variable number/pattern of docking pins, such that the eyewear can determine the intended function of the application module, a type of the application module, and/or variable capabilities of the application module. For example, the eyewear connection points can register circuits, or output, related to any of the pre-configured connection points In embodiments, the application module 100 may be substantially water resistant, sweat resistant, water proof, and/or wear resistant. For example, the casing of the application module 100 may be water proof, and each of the connection points may be sealed, individually or collectively, in a manner to make them water resistant, sweat resistant, water proof, and/or wear resistant. The application module 100 may also be configured to be substantially water resistant, sweat resistant, water proof, and/or wear resistant when mounted to the docking station, eyewear frame and/or a universal connector. For example, the application module 100 may include a gasket or other sealing mechanism around the preconfigured application connection points such that when the application module 100 is mounted to the docking station, eyewear frame and/or a universal connector, the application connection points are substantially water resistant or water proof.

Figure 2A:
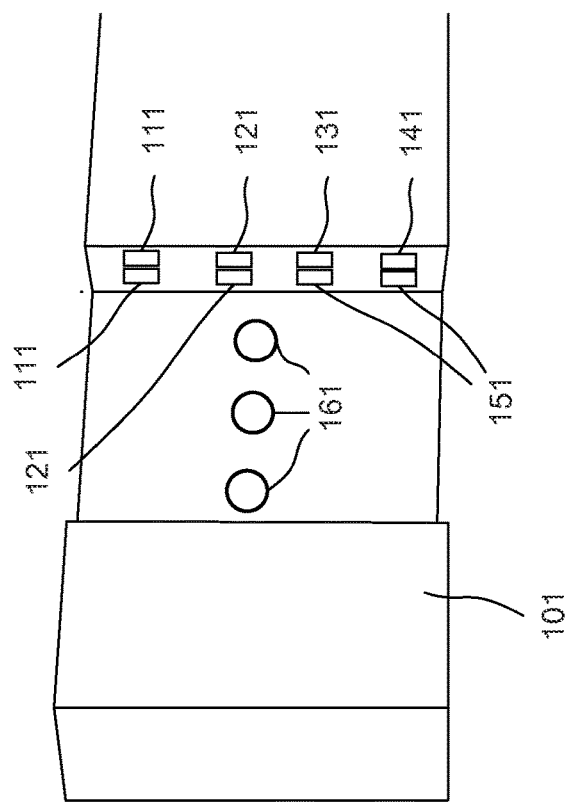
FIG. 2A illustrates a portion of an exemplary eyewear frame temple, including a docking station and connection points in accordance with an aspect of the present invention.
Figure 2B:
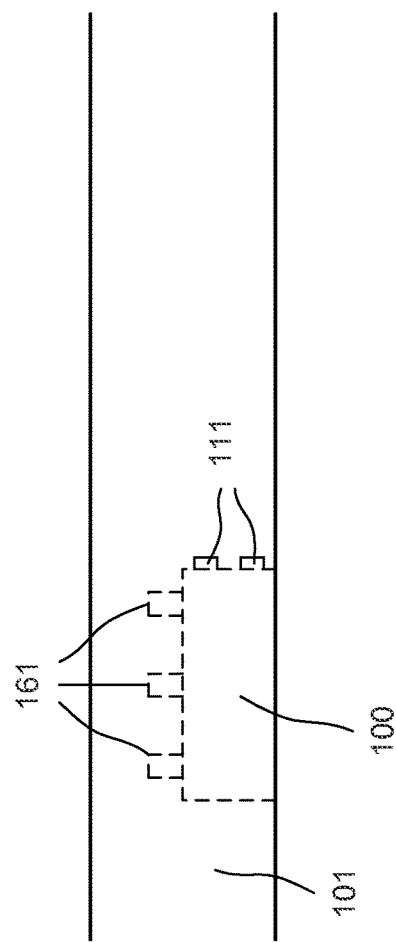
FIG. 2B illustrates a portion of an exemplary eyewear frame temple, such as shown in FIG. 2A, including a docked application module in accordance with an aspect of the present invention.

Additional details regarding possible mounting arrangements for the application module 100 are shown in FIGS. 2A and 2B. FIG. 2A illustrates a portion of an exemplary eyewear frame temple 101, including a docking station and connection points in accordance with an aspect of the present invention, and FIG. 2B illustrates a portion of an exemplary eyewear frame temple, such as shown in FIG. 2A, including a docked application module 100 in accordance with an aspect of the present invention.

As shown in FIG. 2A, an eyewear frame temple portion 101 may include a recessed portion with docking pin recesses 161 corresponding to one or more of docking pins 160. As noted previously, certain embodiments may allow for the eyewear to detect the type of application module via arrangement of pins/recesses or other means. Therefore, although docking pin recesses 161 are shown corresponding to all docking pins 160, it is also possible for there to be different numbers and arrangements of docking pins/recess among different application modules useable by the same docking station.

The recess in eyewear frame temple portion 101 also includes preconfigured application connection points, in this case power connections 111, audio connections 121, audio ground 131, microphone ground 141, and video 151. As noted previously, certain embodiments may allow for different application modules to use only a subset of the connection points included in the docking station of the frame. Therefore, although the connection points in FIG. 2A are shown corresponding to all connection points in module 100, it is also possible for there to be different numbers and arrangements of connection points among different application modules useable by the same docking station.

The preconfigured application connection points included in the recess in eyewear frame temple portion 101 may be configured to directly connect to one or more preconfigured application connection points of the application module when the application module, and/or may be configured to attach to a universal connector cable. The embodiment shown in FIG. 2B represents a possible "direct connect" configuration.

For clarity the eyewear's docking station is capable of receiving one or more application modules specifically designed to be received by said docking station. In certain cases these application modules may comprise their own electrical power required to operate independently of the eyewear's docking station and in other cases one or more of these application modules will not operate properly when not docked within the eyewear's docking means. It should be pointed out that the inventive docking station disclosed herein is associated and located with the inventive eyewear itself and is not intended to be a docking station which the eyewear itself could be docked to down load information, data, or photos to by way of example only, to that of a computer, or to become recharged, or to have the eyewear's software upgraded from a docking station to which the eyewear is docked.

Further, in most cases each application modules has either a similar or identical docking means that fits and provides one or more of the appropriate connectivity (electrical, audio, video, memory) within the eyewear's docking station. However, in certain other cases the docking means located on or near the end of the application device can be of a different design but will still allow for docking and connecting within the eyewear's docking station.

For clarity the term "docking means" as used herein is that of the architecture/engineering design which allows for the application modules to be attached/connected to the docking station. The "docking station" is the station which receives the docking means of an application device.

As shown in FIG. 2B, an application module 100 may be mounted to eyewear frame temple portion 101 in the recessed portion with one or more docking pins 160 inserted in docking pin recesses 161. In this case, the application connection points included in the recess, such as power connections 111, are configured to directly connect to the application connection points (not shown) of the application module 100 when the application module is docked.

Figure 3:
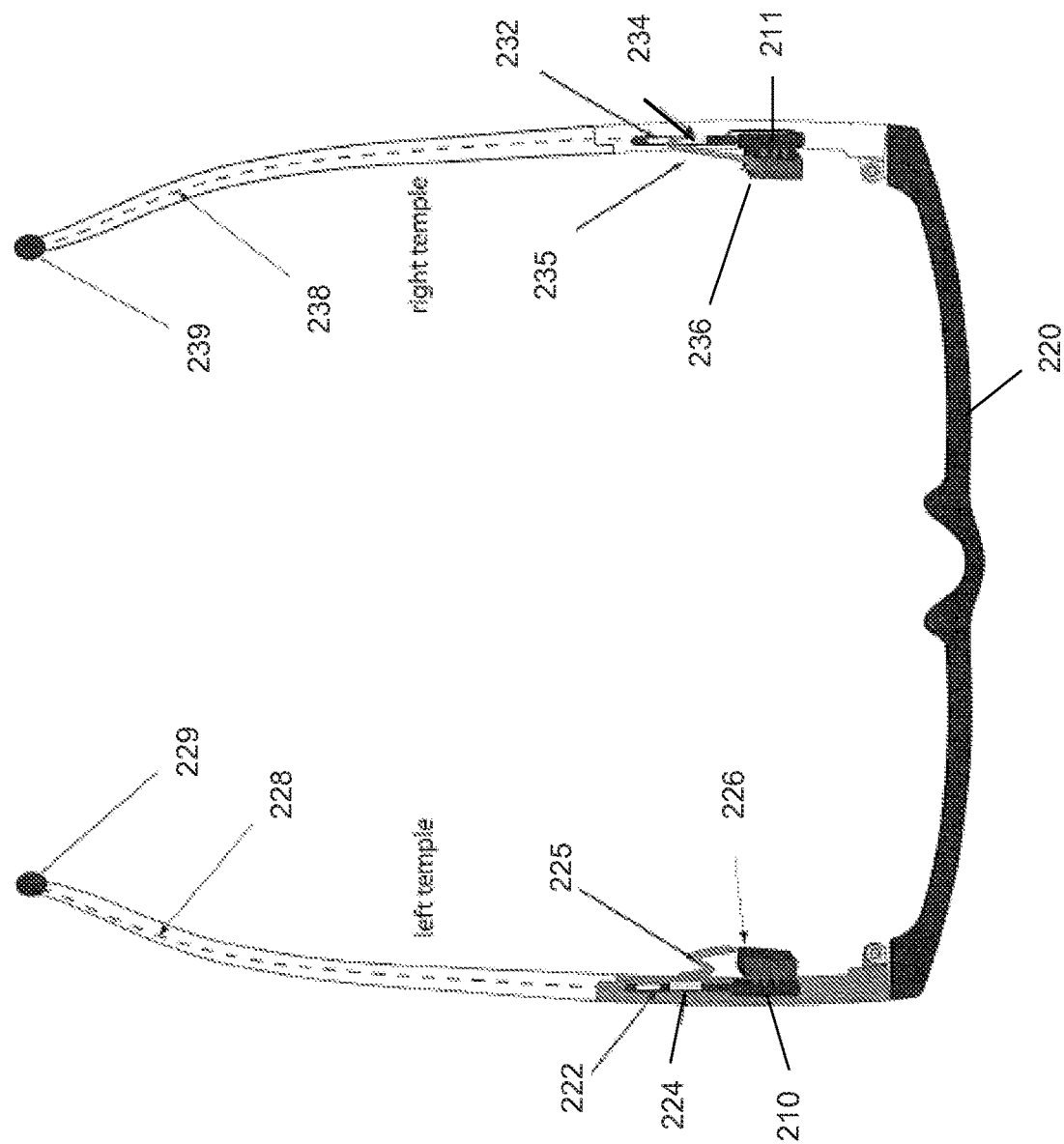
FIG. 3 is a top-down view of an exemplary frame including earbuds and docked application modules connected to connection points of the frame in accordance with an aspect of the present invention.

FIG. 3 is a top-down view of an exemplary frame including earbuds and docked application modules connected to connection points of the frame in accordance with an aspect of the present invention. As shown in FIG. 3, an eyewear system may be provided including an eyewear frame including lens holder 220, and left and right temple portions. Each of the left and right temple portions include a docking station 210, 211, and a docked application module 226, 236, respectively, adapted to be mounted to the docking station. In this embodiment, each of the left and right temple portions also includes an electronic connector 225, 235, respectively, including a first set of preconfigured application connection points and associated conductive paths, configured to connect application connection points of the modules to the eyewear, or more specifically to application connection points of electronics included in the eyewear temple portions.

The electronic connectors 225, 235 may be referred to as intermediate electrical contacts, and can include, for example, plug-and-receptacle electrical contacts. In some embodiments, the intermediate electrical contact is located at one of: a rim of the eyewear, the rear ⅓ of the temple, the middle of the temple, the forward ⅓ of the temple, the rim lock or hinge, of the eyewear, a surface of an eyewear functional member, a frame front of the eyewear, an electronic display, an electronic controller, and/or between the rim and the lens of the eyewear.

FIG. 3 shows an example of how electronic connectors 225, 235 can be connected at one end to the application modules, and at the other end to electronics modules 224, 234 of the eyewear frame. Electronics modules 224, 234 may take many forms as discussed herein, and, like the application modules may include, for example, one or more of audio playback, audio recording, acoustic amplification, acoustic canceling, hearing aid, video playback, video recording, photography, fall detection, alertness monitoring, pedometer, geo-location, pulse detector, wireless communication, virtual reality, augmented reality, gaming, eye tracking, pupil monitoring, lens control, automated reminder, lighting, lasing, and alarm. Preferably, more robust processing may be included in electronics modules of the frame, thereby reducing the size and/or data or power requirements of the docked application module. Electronics modules 224, 234, or other functional devices included in the eyewear, such as electronic lenses, cameras, displays, microphones, speakers, etc., may be referred to as functional member(s) of the eyewear.

The application modules 226, 236 and/or electronics modules 224, 234 may include one or more of still photo camera, video camera, digital audio player, display, projector, hearing aid, fall detector, alertness monitor, pedometer, pulse detector, cell phone, audio system, communication system, video system, music system, audio system, $CO_2$ detector, poor air quality alert device, bad breath detector, thermometer, refractive error measurement device, GPS system, virtual reality system, augmented reality system, gaming system, eye tracking device, pupil monitor device, sensor, smoke detector, pill reminder, medication reminder, speaker, light, laser.

In embodiments, the eyewear frame such as shown in FIG. 3 may include a lens, and the electronic module(s) 224, 234 and/or application module(s) 226, 236 may be configured to at least partially control the lens. For example, the lens may be an electro-active lens and one or more of the modules may be configured to control a focus, tint or other change of the lens based on sensed conditions (such as lighting) and/or user commands. In other embodiments, the lens may have built in display functions that can be controlled by one or more of the modules, such as with virtual or augmented reality, or gaming.

In embodiments, the eyewear lens may be one of a dynamic focusing lens, static focusing lens, tinted lens, photochromic lens, electrochromic lens, thermochromic lens, or display.

In embodiments, the eyewear frame may include a speaker, such as earbuds 229, 239, and one or more of the modules may be configured to provide an audio signal to the speaker(s) via audio connectors 228, 238. In certain embodiments, each of application modules 226, 236 may be configured to independently provide audio, lens adjustment, video, etc. to the respective speaker, lens etc. associated with that side of the frame. For example, individually tailored hearing aid functions, prescription adjustment or augmented reality may be independently provided. In embodiments, the customization provided may be improved, at least in part, by independent programming included in electronics modules 224, 234, e.g. different hearing adjustment, or visual correction, while using a standard, functionally equivalent, application module 226, 236.

In embodiments where the eyewear frame includes at least one of a speaker and a lens, the electronic device may be configured to provide at least one of virtual reality and augmented reality to a user via the speaker and/or lens.

The frame shown in FIG. 3 also includes power sources 222, 232 in each of the temple portions. The power sources 222, 232 may be connected to application modules 226, 236 to provide operating and/or rechargeable power. However, it should be noted that a single power source may be used to power the one or more application modules etc. The power source(s) may include, for example, one or more of a rechargeable battery, disposable battery, fuel cell, solar cell, or kinetic energy source whereby movement of the eyewear generates power.

As noted previously, the docking station and/or application module may be configured to convert the application module from a non-functioning application module into that of a functioning application module upon being docked to said docking station. For example, the application modules 226, 236 may be configured such that they are dependent on one or more of power, sensor input, audio input and/or video input from the eyewear frame, or other source, in order to function.

In embodiments, the application modules 226, 236 may be utilized more than one at a time while the eyewear is being worn by a wearer and/or may include different functionality.

In embodiments, the eyewear such as shown in FIG. 3 may further include a controller, such as included in electronics modules 224, 234, configured to be connected to the application modules 226, 236, and to provide command signals and/or programming to the application modules 226, 236.

In some embodiments, the eyewear frame can include a temple and a rimlock. In those embodiments, a functional member of the eyewear can be located in the temple, and a connective element can be routed from the application module through the rimlock to the optical functional member. In some embodiments, the rimlock includes an upper rimlock and a lower rimlock, and the connective element is routed between the upper rimlock and the lower rimlock. The rimlock can include upper rimlock and a lower rimlock, and the connective element can form a layer between the upper rimlock and the lower rimlock. The layer can be insulating. In some embodiments, the connective element can be a conductive compressible member that can be conductive rubber. In some embodiments, the connective element comprises a multi-conductor cable.

The eyewear of FIG. 3 may include electro-active spectacles or eyeglasses in accordance with an aspect of the present technology. Thus, the spectacles shown in FIG. 3 may be eyeglasses comprising left and right temples and a frame front (the frame front can comprise left and right eyewires or rims, and a bridge, as will be appreciated by one skilled in the pertinent art). Electro-active spectacles and frames of the present technology can be fully rimmed, partially rimmed, or rimless. The spectacles can include a first electro-active lens, and a second electro-active lens. The first and second electro-active lenses can each be an electro-active lens such as described, for example, in U.S. patent application Ser. No. 12/408,973 (hereinafter the '973 application), filed Mar. 23, 2009, entitled "Electro-Active Diffractive Lens and Method for Making the Same," which is hereby incorporated by reference in its entirety. In general, the first and second electro-active lenses can be any lens or optic capable of changing, varying or tuning the optical power they each provide with the application of electricity.

The right temple portion can be considered to be a first temple portion that is positioned adjacent to the first electro-active lens. The left temple portion can be considered to be a second temple portion that is positioned adjacent to the second electro-active lens. The bridge can be considered to be part of the frame or to be a separate portion of the spectacles that connects, joins or supports the first and second electro-active lenses. The spectacles can include one or more power sources, e.g. 222, 232 or others, for powering the first and second electro-active lenses. As an example, each power source can include one or more batteries (e.g., conventional rechargeable batteries and/or solar batteries). The spectacles can also include electronics, such as in electronics modules 224, 234, or included in the application modules 226, 236, that can govern operation of the electro-active lenses. The electronics can comprise one or more control units (e.g., a control unit matched to each electro-active lens) to determine when to activate and when to deactivate the electro-active lenses. The one or more power sources and the electronics of the spectacles can be housed or contained within, or on, any portion of the frame or included in the application modules 226, 236. The one or more power sources and the one or more control units of the spectacles can be grouped together or distributed or dispersed in any manner within, throughout, or on the frame or included in the application modules 226, 236.

The operation of the electro-active lenses can be synchronized (even if independently programmed). That is, the one or more control units housed in the frame or included in the application modules 226, 236, can coordinate the activation and deactivation of the electro-active lenses such that the electro-active lenses are activated or deactivated at substantially the same time.

The one or more control units housed in the frame or included in the application modules 226, 236, can automatically operate (e.g., activate and deactivate) the electro-active lenses 104 and 106. As an example, the electro-active lenses 104 and 106 can be activated or deactivated based on a user's head tilt as sensed by the one or more control units. The one or more control units can also enable a user to interact with the electro-active lenses 102 and 104. As an example, a user can manually activate or deactivate the electro-active lenses 104 and 106, override automatic operation of the electro-active lenses 104 and 106, place the electro-active spectacles 100 into a standby mode (in which the electro-active lenses 104 and 106 are neither automatically or manually activated or deactivated), or power off the electro-active spectacles 100.

The electronics of the electro-active spectacles can include a processor, memory, a power source (e.g., a battery), a gyroscope, and an accelerometer. As previously mentioned, these components can be grouped together or can be distributed within different portions of the frame or included in the application modules 226, 236. As an example, all or a portion of these components can be grouped together to form a self-contained electronic module. The electro-active spectacles can comprise a single electronic module that governs synchronized operation of both the first and second electro-active lenses. Alternatively, operation of the first electro-active lens can be governed by a first electronic module and operation of the second electro-active lens can be governed by a second electronic module. Under this scenario, the first and second electronic modules may be configured to communicate using one or modes of electrical connectivity (e.g., wire(s) embedded within a portion of the frame, conductive portion(s) of the frame, conductive metal layer(s) or core(s) encapsulated by non-conductive material, conductive layer(s) of the electro-active lens(es), optical link(s), wireless radio frequency or magnetic field communication).

It is noted that, in some cases, only one docking station may be provided with the eyewear, whereas in other embodiments multiple docking stations may be provided. In one preferred embodiment of the invention one temple may be utilized for housing an electronic module which controls or alters the optics and/or tint of the eyewear's lenses and a docking station is located on, partially in, or fully embedded in the other temple. In another preferred embodiment of the invention one temple is utilized for housing an electronic module which controls or alters the optics and/or tint of the eyewear's lenses, and a docking station is located on, partially in or fully embedded within the other temple. In yet another embodiment, such as shown in FIG. 3, two docking stations are provided such that, by way of example only, one can be located with the right temple and one located with the left temple. By way of example only, one example of such eyewear utilizing two docking stations is the use of two cameras; one located in each docking station for the purposes of providing 3D photos, or video. In certain cases when two cameras are utilized a prism lens or lenses may associated such to spread out the horizontal distance angle of the object which the camera are taking a picture of Another example would be the use of two docking stations, one on each temple to provide attachable, detachable hearing aids. And still another example only, would be the use of two docking stations to provide attachable, detachable speakers which could then be adjusted to be positioned in or near each of the wearer's ears. The speakers can be those of earbuds and can be spring loaded retractable and/or extendable.

The inventive docking means allows for one or two hearing aids to be used by the wearer. In certain embodiments one hearing aid application device module drives two earbuds or speakers (one in each end of the temple). In another embodiment two hearing aid application device modules each drive one earbud or speaker. Thus both are provided for the wearer but each earbud or speaker is driven by one hear aid application device module.

Figure 4:
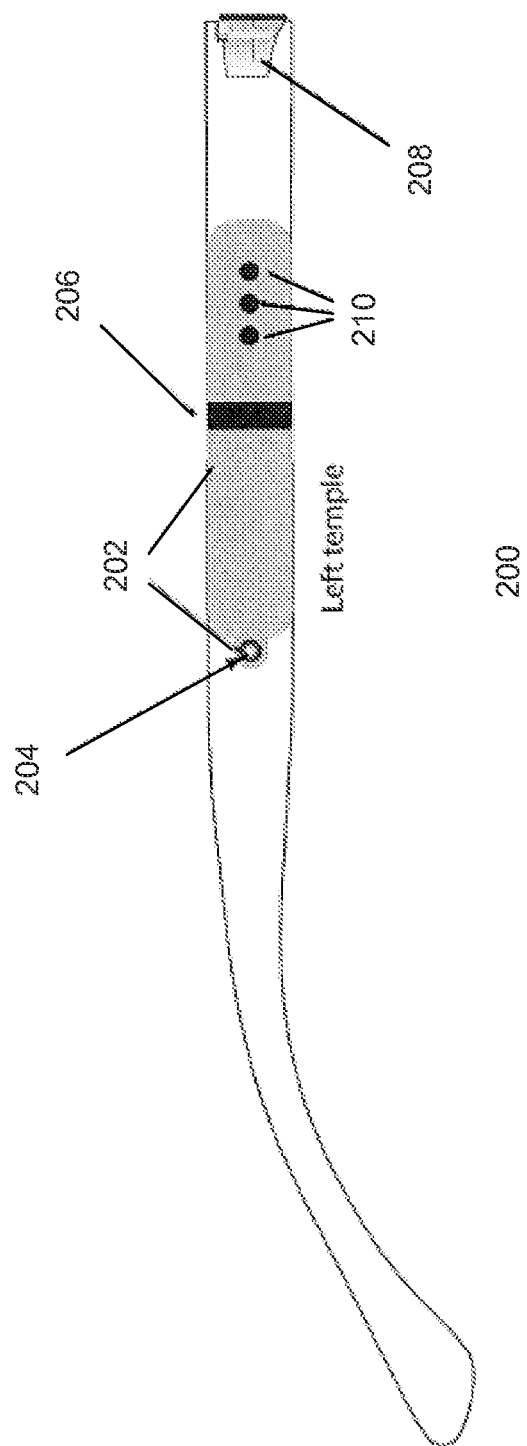
FIG. 4 illustrates a portion of a frame including a docking station in accordance with an aspect of the present invention.

FIG. 4 illustrates a temple portion of a frame including a docking station in accordance with an aspect of the present invention. FIG. 4 may be understood as illustrating a side view of a left temple portion with a hinge portion 208, with some similar features to that depicted in FIG. 3. As shown in FIG. 4, the temple portion can comprise a docking station 210, a cover 202 for covering internal electronic components of the temple portion (e.g. the electronics module 224, power source 222 and/or preconfigured connection points as described herein. In the embodiment shown in FIG. 4, an access door 206 for accessing the preconfigured connection points is closed.

Figure 5:
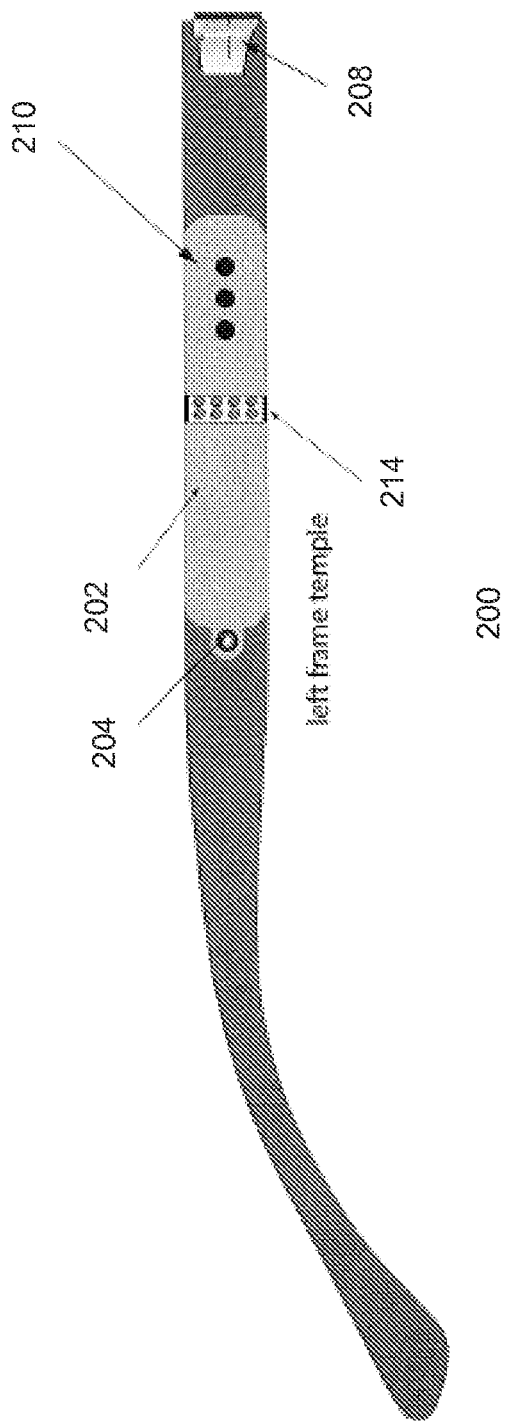
FIG. 5 illustrates a portion of a frame including a docking station and exposed connection points in accordance with an aspect of the present invention.

FIG. 5 illustrates the temple portion shown in FIG. 4, with the access door 206 opened. In this view, the access door 206 is opened for accessing the preconfigured connection points 214 such that the universal connector cable may be attached to the electronics module of the eyewear, or such that a properly configured application module may be directly connected to the preconfigured connection points.

Figure 6:
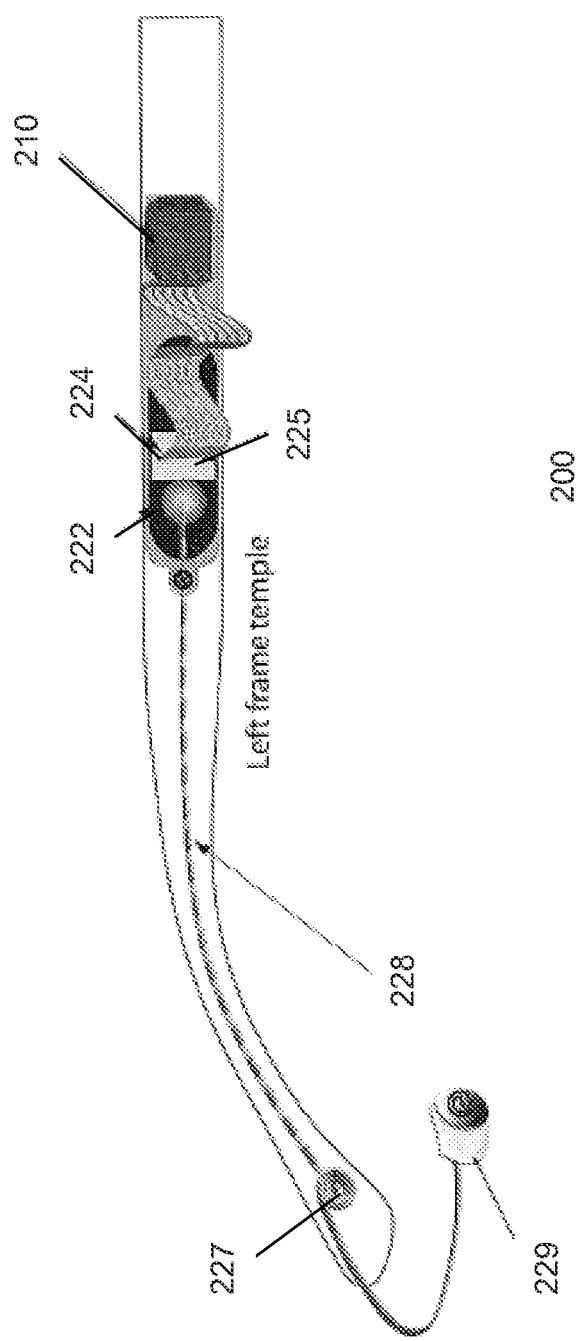
FIG. 6 illustrates a portion of a frame including an earbud and a docked application module connected to connection points of the frame using a universal connector in accordance with an aspect of the present invention.

FIG. 6 is a partial cut away view illustrating a temple portion of a frame including a docked application module docked to docking station 210 in accordance with an aspect of the present invention. As shown in FIG. 6, an application module may be docked to docking station 210, and connected to connector 225 with cover 202 at least partially opened. The internal electronics module 224, power source 222 are also shown. In the embodiment shown in FIG. 6, the temple portion 200 also includes retractable earbud speaker 229 with a spring loaded connector 227 and audio path 228.

Figure 7:
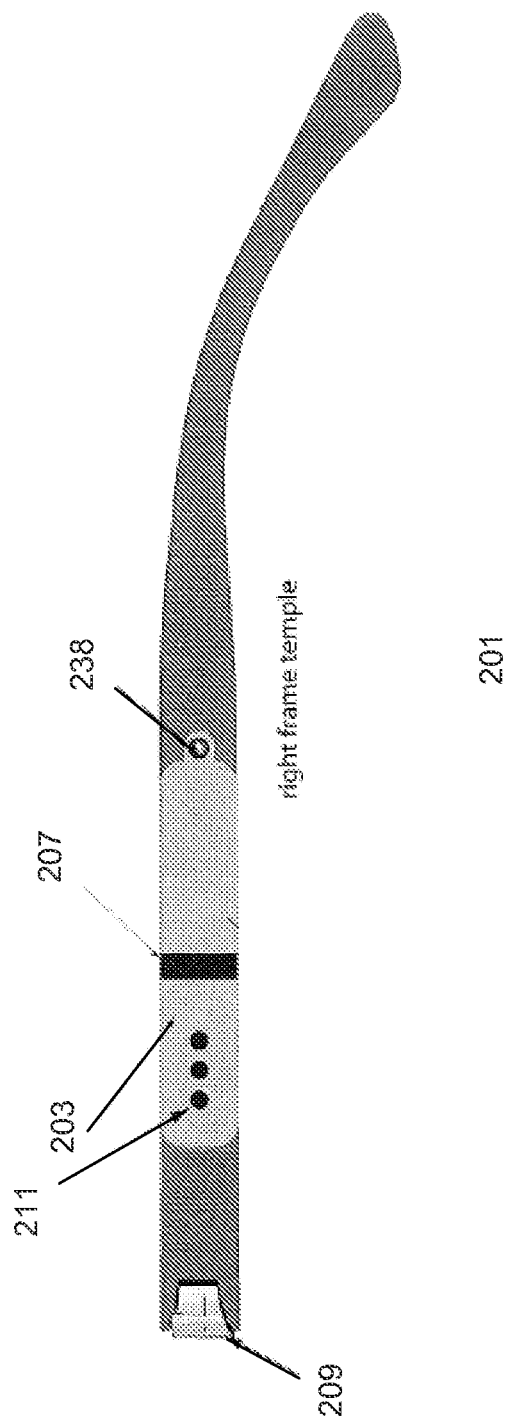
FIG. 7 illustrates a portion of a frame including a docking station in accordance with an aspect of the present invention.

FIG. 7 illustrates a right temple portion 201 of a frame including a docking station in accordance with an aspect of the present invention. FIG. 7 may be understood as illustrating a side view of an opposite temple portion from that shown in FIG. 4, with a hinge portion 209. As shown in FIG. 7, the right temple portion can comprise a docking station 211, a cover 203 for covering internal electronic components of the right temple portion (e.g. the electronics module 234, power source 232 and/or preconfigured connection points as described herein. In the embodiment shown in FIG. 7, an access door 207 for accessing the preconfigured connection points is closed.

Figure 8:
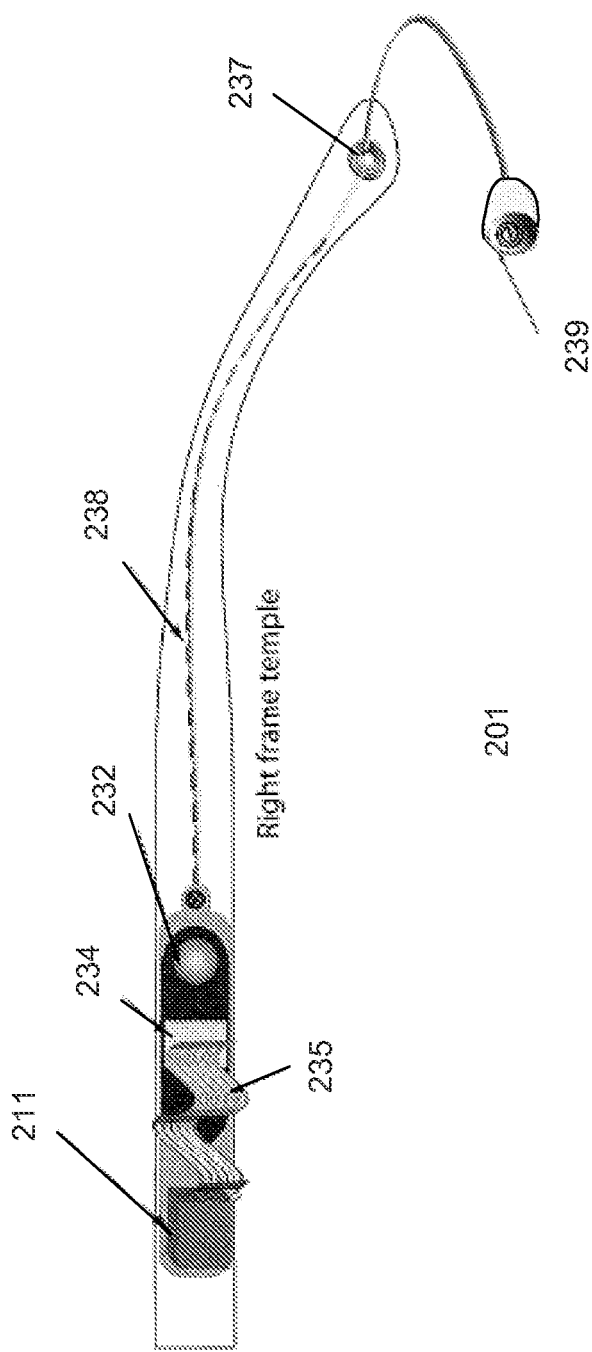
FIG. 8 illustrates a portion of a frame including an earbud and a docked application module connected to connection points of the frame using a universal connector in accordance with an aspect of the present invention.

FIG. 8 is a partial cut away view illustrating a temple portion of a frame including a docked application module docked to docking station 211 in accordance with an aspect of the present invention. As shown in FIG. 8, an application module may be docked to docking station 211, and connected to connector 235 with cover 207 at least partially opened. The internal electronics module 234, power source 232 are also shown. In the embodiment shown in FIG. 8, the temple portion 201 also includes retractable earbud speaker 239 with a spring loaded connector 237 and audio path 238.

It should be noted that the temple portions illustrated in FIGS. 4-8 may be configured to partially or fully receive the application module, or to mount the application module without receiving any portion of the application module. In embodiments, where the application module is fully received in the temple portion, it may be covered by a slidable cover such as 202.

As described above, the electronic module of the frame such as 224, 234, can include various electronics components. The electronic module 224, 234 can be positioned near the front temple of the frame. The electronic module 224, 234 can be positioned within the frame (e.g., in an area or cavity of the frame) and can be removable and replaceable. Alternatively, the electronic module 224, 234 can be built into the frame and form a part of the frame. The electronic module 224, 234 can be located on an outer portion of a temple of the frame (further from a wearer) or can be located on an inner portion of the temple of the frame (closer to the wearer). The electronic module can be positioned on a left temple or a right temple of the frame (i.e., on either side of the frame). The electronic module 224, 234, when inserted into the temple of the frame, can be flush with the other portions of the frame. All or a portion of the electronic components used to operate electro-active lenses or other eyewear functional members can be contained within the electronic module.

In some embodiments of the present technology, a first electrical connection (e.g., comprising one or more conductive links or wires) can be used to provide connectivity between one or more power sources of spectacles and one or more electronic modules and a second electrical connection (e.g., comprising one or more conductive links or wires) can be used to provide connectivity between one or more electronic modules and one or more electro-active lenses (e.g., electro-active lenses). For example, a battery positioned within the frame can be coupled to an electronic module also positioned within the frame using a first conductive link. A second, distinct conductive link (e.g., electrically isolated from the first conductive link) can be used to couple the electronic module to the electro-active lenses.

Figure 9:
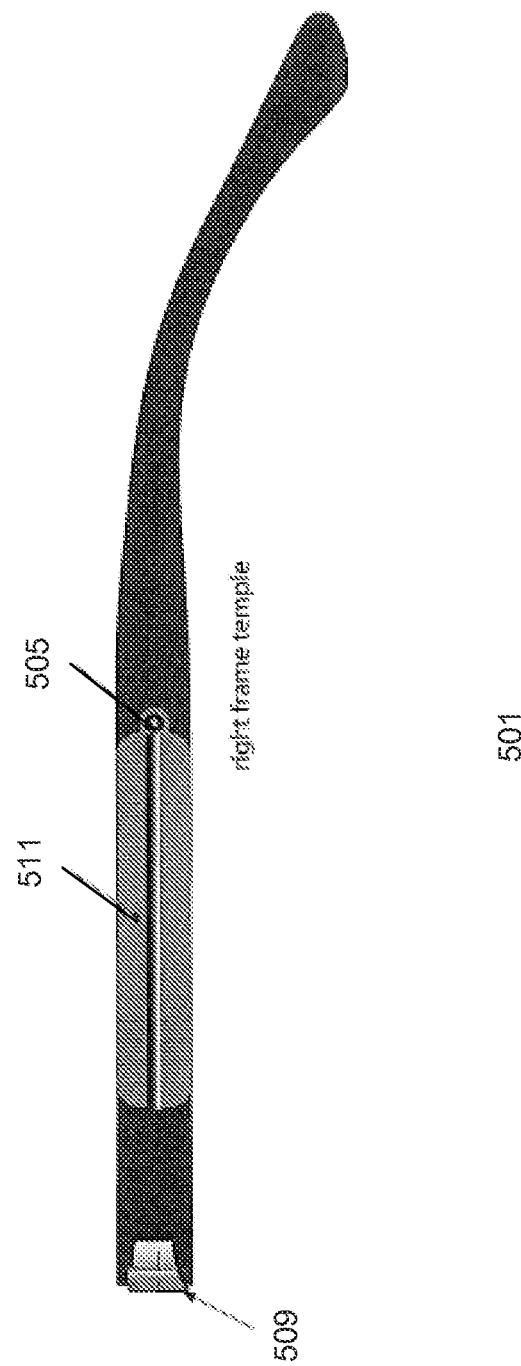
FIG. 9 illustrates a portion of a frame including a docking station track in accordance with an aspect of the present invention.

FIG. 9 illustrates a right temple portion 501 of a frame including a track docking station 511 in accordance with an aspect of the present invention. FIG. 9 may be understood as illustrating a side view of a temple portion, with a hinge portion 509. As shown in FIG. 9, the right temple portion can comprise a track docking station 511, with a release mechanism 505 for releasing a docked application module (not shown) and/or adjusting a cover over the track. In the embodiment shown in FIG. 9, the preconfigured connection points may be included inside the mounting track and a plurality of application modules may be mounted to and/or adjusted along the track. All or part of the track may be covered by a moveable cover via actuation of the release mechanism 505.

Figure 10:
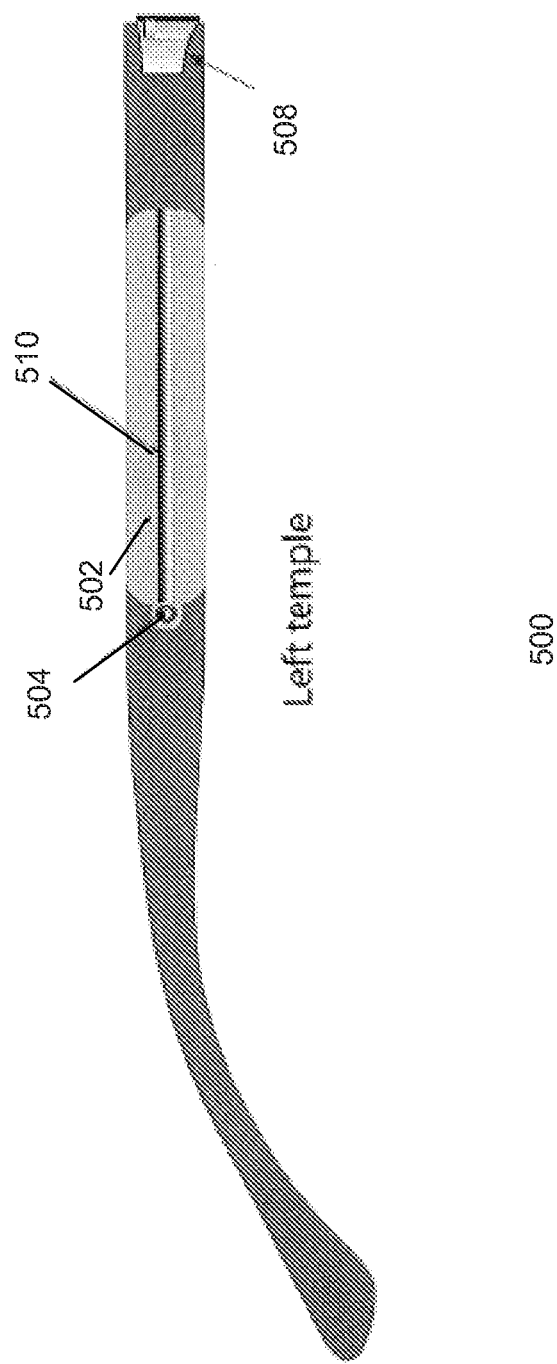
FIG. 10 illustrates a portion of a frame including a docking station track in accordance with an aspect of the present invention.

FIG. 10 illustrates a left temple portion 500 of a frame including a track docking station 510 in accordance with an aspect of the present invention. FIG. 10 may be understood as illustrating a side view of a temple portion, with a hinge portion 508. As shown in FIG. 10, the left temple portion can comprise a track docking station 510, with a release mechanism 504 for releasing a docked application module (not shown). In the embodiment shown in FIG. 10, the preconfigured connection points may be included inside the mounting track 502 and a plurality of application modules may be mounted to and/or adjusted along the track.

Figure 11:
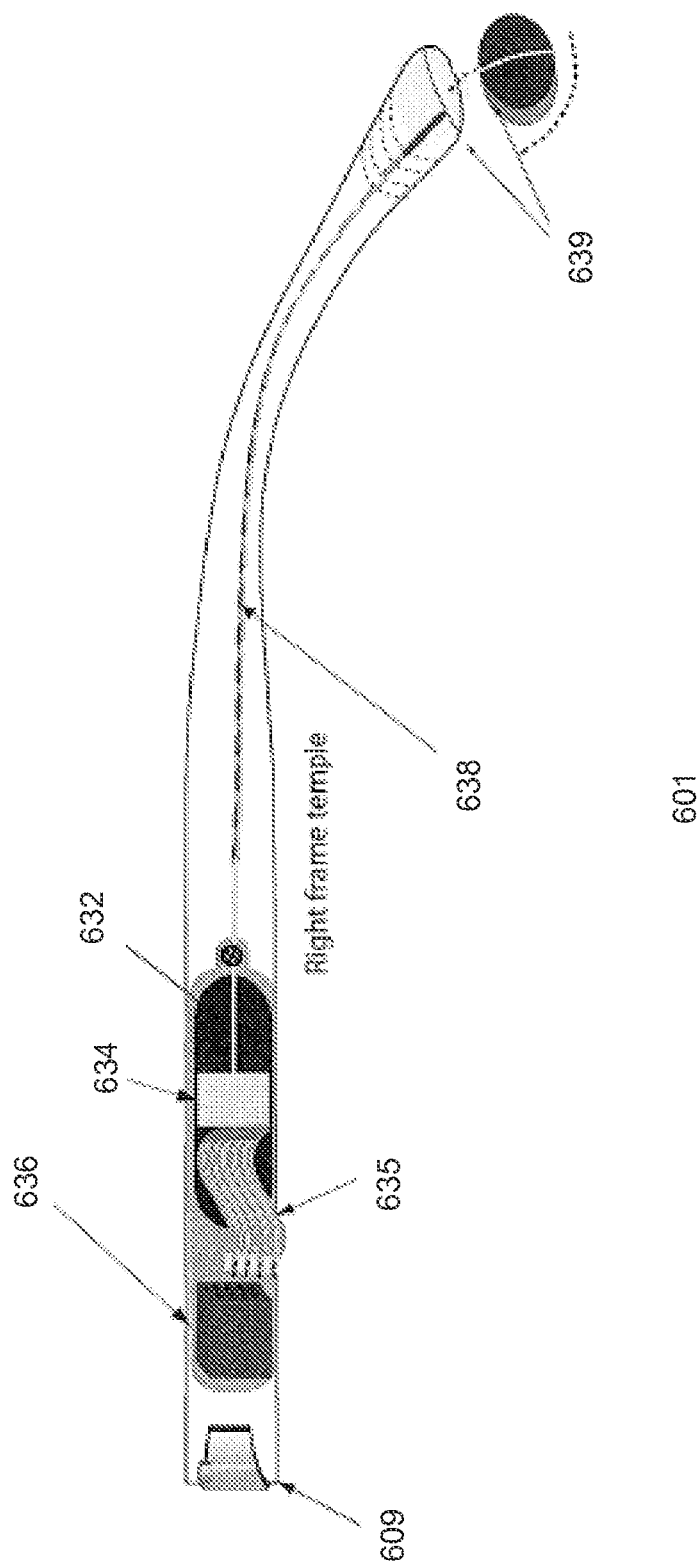
FIG. 11 illustrates a portion of a frame including a docked application module and a removable functional member in accordance with an aspect of the present invention.

FIG. 11 illustrates a right temple portion 601 of a frame including a docking station in accordance with an aspect of the present invention. FIG. 11 may be understood as illustrating a side view of a right temple portion, with a hinge portion 609. As shown in FIG. 11, the right temple portion can comprise a docked application module 636, electronics module 634, power source 632 and/or preconfigured connection points as described herein. In the embodiment shown in FIG. 11, supplemental power source 639, which may be removable, is also included at an end of the temple portion and connected to the eyewear electronics via conductor 638. In embodiments, the supplemental power source 639 may be, instead a memory, or other supplemental device.

Figure 12:
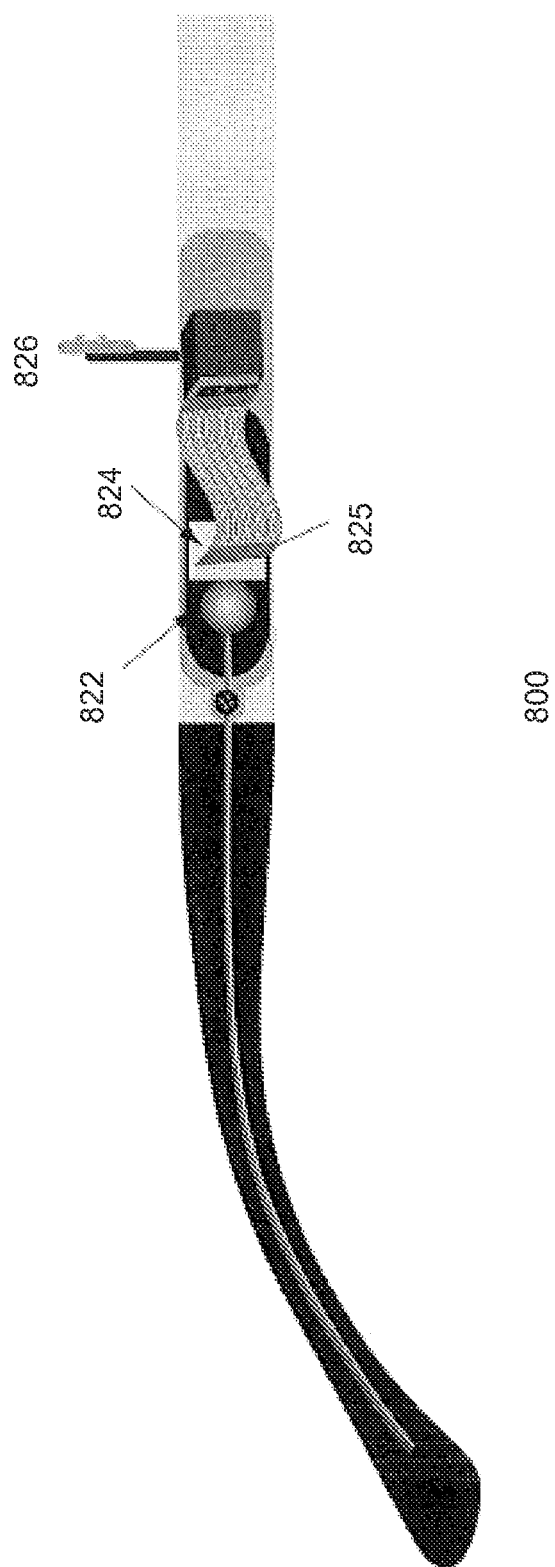
FIG. 12 illustrates a portion of a frame including a docked application module camera connected to connection points of the frame using a universal connector in accordance with an aspect of the present invention.

FIG. 12 illustrates a left temple portion of a frame including a docked camera 826. Camera 826 may be configured for capturing still images or video, or may simply provide an optical path, e.g. fiber optics, for camera circuitry included in the frame. Camera 826 may include a microphone as well for audio recording. As shown in FIG. 12, the temple portion can comprise a docked camera 826, electronics module 824, power source 822 and/or preconfigured connection points as described herein. It should be appreciated that a similar right temple portion may also be provided for stereoscope imaging.

Figure 13:
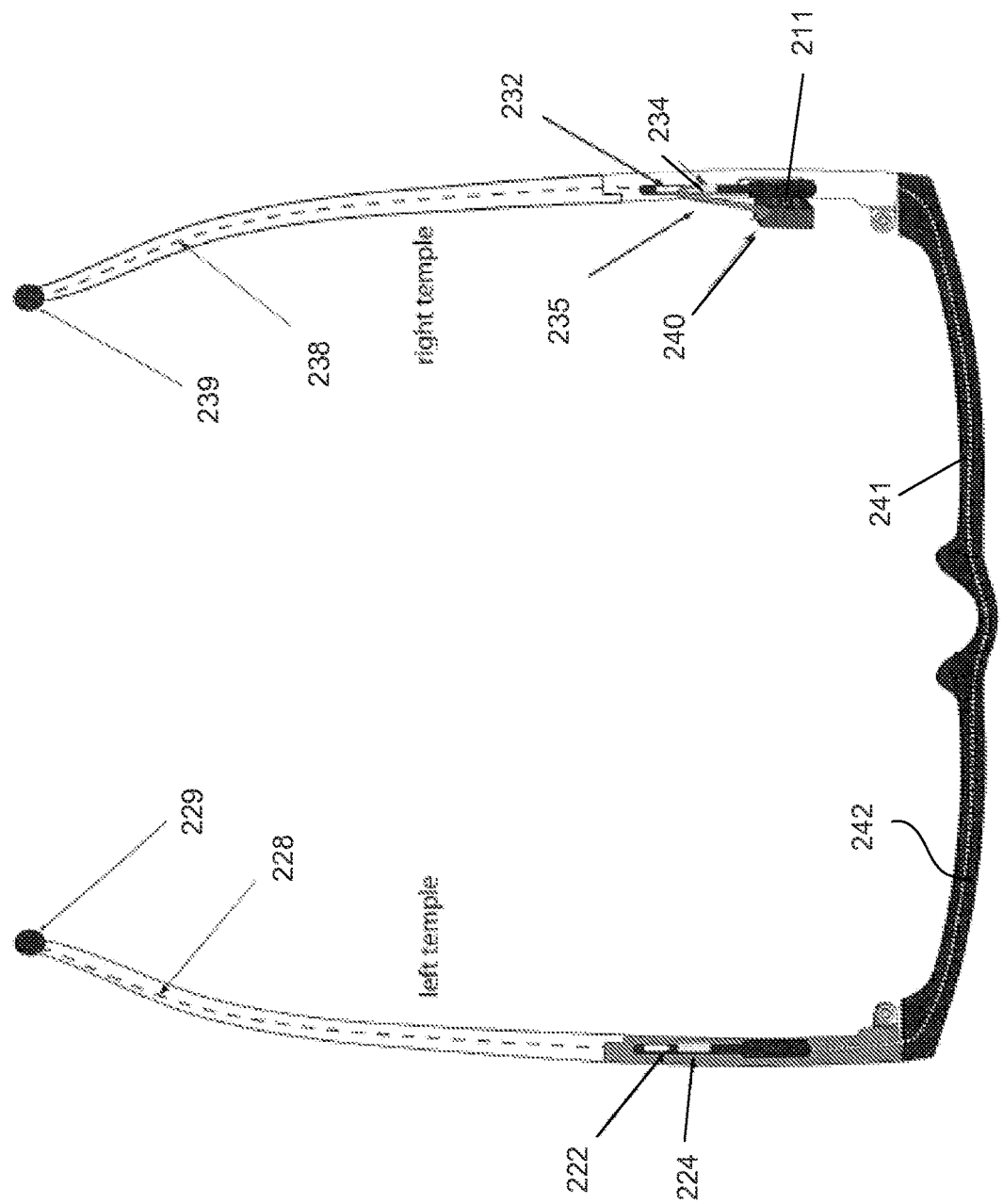
FIG. 13 is a top-down view of an exemplary frame including a docked application module that is connected to connection points on one side of the frame, and in communication with electronics on an opposite side of the frame, in accordance with an aspect of the present invention.

FIG. 13 is a top-down view of an exemplary frame including earbuds and a single docked application module connected to connection points of the frame in accordance with an aspect of the present invention. As shown in FIG. 13, an eyewear system may be provided including an eyewear frame including lens holder 241, and left and right temple portions. Right temple portion include a docking station 211, and a docked application module 240, adapted to be mounted to the docking station. In this embodiment, the right temple portions includes an electronic connector 235, including a first set of preconfigured application connection points and associated conductive paths, configured to connect application connection points of the module to the eyewear, or more specifically to application connection points of electronics 234 included in the eyewear temple portion. In this embodiment, a connector 242 is also included for simultaneous control of left temple functional members by the application module 240, e.g. electronics 224, or speaker 229 via audio connection 228, while controlling right temple functions via electronics 234, speaker 239 via audio connection 238. Application module 240 may be powered by either or both of power sources 222, 232.

As further shown in FIG. 13, the frame can include conductive leads 228 and 238 and conductive link 242. Conductive link 242 can provide electrical connectivity from one side of the frame to the other side of the frame. The conductive link 242 can be embedded or positioned within the frame. The conductive link 242 can include any number of conductive elements (e.g., wires) that can be insulated or not insulated. If the frame uses driver electronics on each side of the frame (e.g., a master and slave driver electronics or electronic modules) then as few as only one single wire can comprise the conductive link). If the frame has driver electronics on only one side of the frame, then at least two wires or conductive elements can be used. The conductive link can be positioned inside the frame in accordance with any suitable methods for embedding conductive links including, but not limited to, (1) embedding during a mold casting process; (2) embedding during an assembly process of the front frame portion of the frames; and (3) embedding after assembly of the frames by providing a groove or route for the conductive link. The conductive link can also use or can alternatively comprise the conductive layers of the lenses of the present technology that can be positioned into the frames.

The docking station can comprise a wireless communication component, such as a Bluetooth chip or circuit, such to enable wireless communication between the docked application device module (application module) and a remotely located device, such as by way of example only, cell phone, smart phone, computer, automobile, iPad, tablet, watch, television, security system, radio. The application module which is docked within the docking station can comprise a wireless chip of circuit such to enable wireless communication between the docked application device module (application module) and a remotely located device, such as by way of example only, cell phone, smart phone, computer, automobile, iPad, tablet, watch, television, security system, radio. When the application device (application module) comprises the wireless chip or circuit it is not necessary that the docking station comprise such a chip or circuit. Various wireless means are well known and understood in the communication art. Bluetooth 4.0 is low power with a communication range of 30 feet or less. In the invention, Bluetooth 4.0 has been shown to be highly effective allowing either wireless communication from the docking station to a remote Bluetooth enabled device or from the application device module to a Bluetooth enabled device. While the invention disclosure teaches Bluetooth 4.0 it should be understood that this invention disclosure anticipates new evolving Bluetooth versions that will come in the future and is not intended to be limited to Bluetooth 4.0 or for that matter Bluetooth. Any and all wireless communication protocol (including by way of example only, RFID) is meant to be included within the scope of the patent application and can be included within the application device module (which can be docked within the docking station), within the docking station, (one of the other or both).

In one embodiment of the invention the wearer of the wireless enabled eyewear comprising either the wireless chip or circuit being comprised within the docking station or the application device module docked in the docking station walks into (by way of example only, his or her home after being at work all day) and the remote wireless enabled devices located within his or her home communicate and recognize the presence of the wearer. Upon such recognition the remote wireless enabled devices located with the home can do one or more of the following: adjust the light, temperature, audio devices, video devices to that of the wearer's predetermined desires upon the entry of the wearer into his or her home. In another embodiment of the invention the wearer of the wireless enabled eyewear enters his or her automobile and the remote wireless enabled devices located within the automobile can (by way of example only) do one or more of the following: adjust the seat, radio, temperature, limit maximum speed, awake wearer should wearer fall asleep. In another embodiment of the invention the wearer of the wireless enabled eyewear enters his or her password, turns on his or her computer and the remote wireless enabled devices located within the computer can (by way of example only) do one or more of the following: adjust the brightness, volume, font size, access email. In still another embodiment of the invention one application device module docked within the docking station comprising a wireless chip or circuit communicates wirelessly with another application device module comprising a wireless chip or circuit such that a function of the eyewear can be wirelessly enabled. By way of example only, one hearing aid located on the right temple of the eyewear communicated with a hearing aid located on the left temple of the eyewear.

For clarity it is important to point out that the invention disclosed herein allows for the application module to not only communicate wirelessly with a remote wireless enabled device, but also at the same time provide the desired functionality for the wearer by way of the application device module which is docked within the docking station. By way of example only, an application module being that of a wireless enabled personal assistant module docked within the docking station of the inventive eyewear (upon a verbal question raised orally by the wearer of the inventive eyewear about the weather) by way of a miniature microphone, voice recognition chip contained within the personal assistant device module and also a wireless chip or circuit also contained within the personal assistant device module could communicate to the wearer's wireless enabled computer or smart phone to address any number of questions of the wearer. By way of example only, to look up the weather on the internet wirelessly and then answer the question about the weather through the speakers or ear buds located within the inventive eyewear. In this case certain of electrical power and audio are provided by the inventive eyewear located within the electronic module or somewhere else in the inventive eyewear, while the application device module being that of a personal assistant provides for its specialized functionality, In certain other cases/embodiments all functionality (including electrical power, audio, voice recognition, Bluetooth capability) is provided by the application device module. Needless to say the diversity of various question such a personal assistant can address are almost limitless. In addition, the wireless enabled personal assistant device module docked within the docking station of the inventive eyewear can be used to provide direction by the wearer of the eyeglasses such that the wearer provides an oral command and the wireless enabled personal assistant communicates wirelessly to a remote wireless enabled device to perform a function; such as by way of example only; change a TV station, radio station, increase the temperature of a room, turn on the car, turn up or down a light, alter the tint of the inventive eyewear, alter the focus of the inventive eyewear. Finally, the invention (in certain embodiments) further contemplates that the wireless enabled personal assistant device module may require the wearer to orally enter a security code of some kind before the personal assistant device module will function properly for certain tasks or for all tasks.

Figure 14:
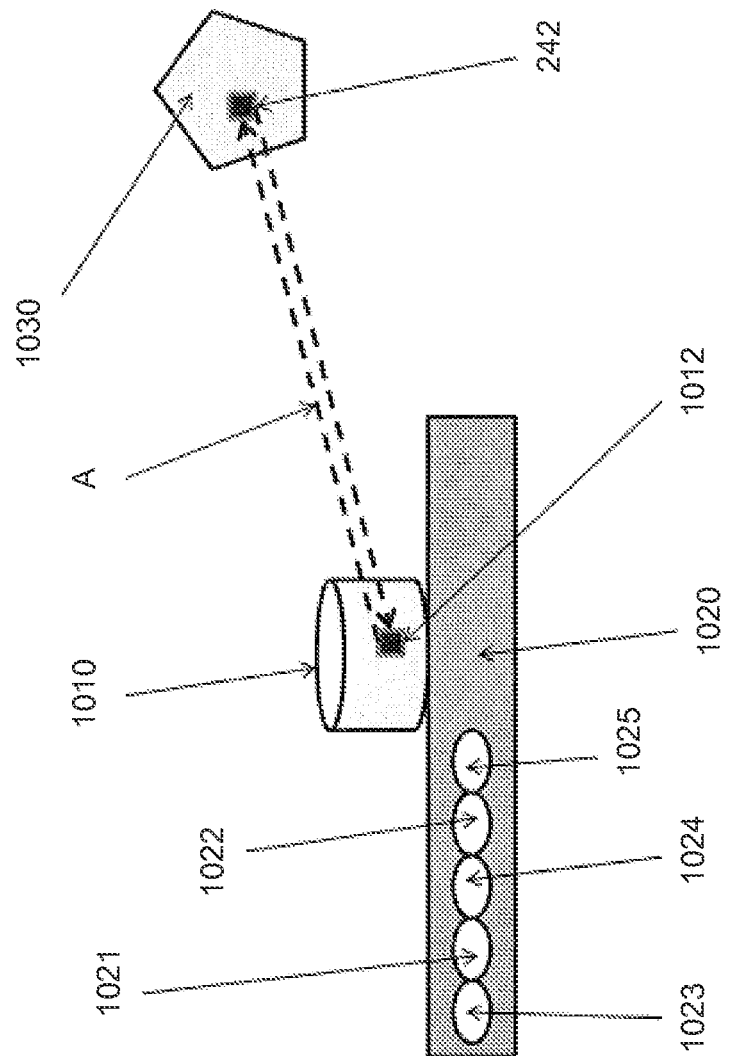
FIG. 14 is a schematic diagram of an electronics module including a wireless transceiver in accordance with an aspect of the present invention.

FIG. 14 provides a high level illustrative rendering of a Bluetooth enabled application device module 1010 docked within the inventive eyewear docking station 1020 communicating wirelessly with a remote Bluetooth enabled device 1030 hereby the Bluetooth enabled application device module 1010 communicates to a remote Bluetooth enabled device 1030 and whereby the remote Bluetooth enabled device 1030 communicates back to the Bluetooth enabled application device module 1010. In addition, it shows that the docking station 1020 provides one or more of audio 1023, video 1024, data 1022, memory 1025, electrical power 1021 to the application device module 1010 that is docked in the docking station 1020. FIG. 14 provides a high level illustrative rendering of a Bluetooth enabled application device module docked within the inventive eyewear docking station communicating wirelessly with a remote Bluetooth enabled device whereby the Bluetooth enabled application device module communicates to a remote Bluetooth enabled device giving directing it to do something. In addition, it shows that the docking station provides one or more of audio, video, data, memory, electrical power to-the application device module that is docked in the docking station.

Figure 15:
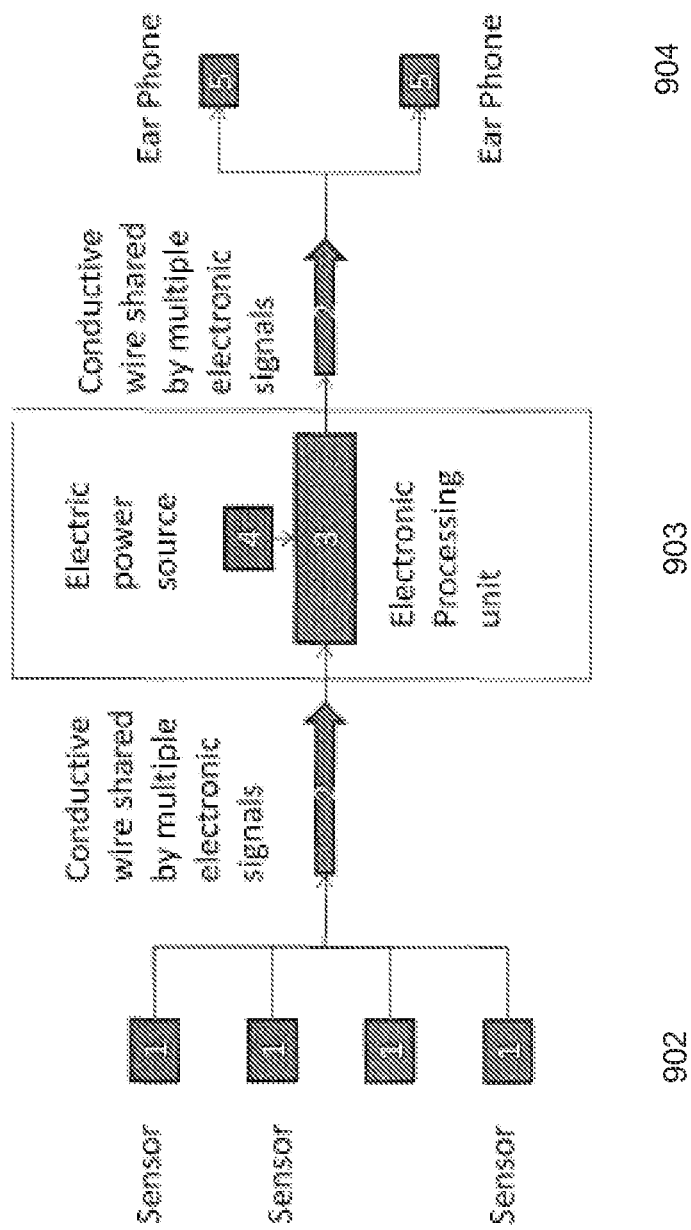
FIG. 15 is a schematic diagram of portions of an eyewear system in accordance with an aspect of the present invention.

FIG. 15 illustrates additional details regarding an exemplary acoustic processor that may be included in embodiments of the invention. In FIG. 15, Block 902 represents sensors including an acoustic wave sensor. One or more acoustic wave sensors are attached to or embedded in the several locations of the frame, left and right temples in order to collect acoustic signals from different directions. The sensor(s) can converts the acoustic signal from environment into a digital or analogue data signal which can be processed by an electronic processing unit 903. Multiple acoustic sensors can collect more environment sound information from different distances and directions, and allow the electronic processing unit to improve the quality of the sound heard by user. These sensors can be placed in different locations in the front of the eyeglass frame near the temples and nose-bridge.

The said digital or analogue data signals may be sent to the electronic processing unit 903 through conductive wires which can be attached to or embedded in the frame and/or temple. The conductive wires can also be the parts of the frame and/or temples. These wires can provide drive signals to the speakers or earbuds or to the lenses. Signals can be separated by high pass filters, low pass filters, or a combination thereof.

A power source as described herein may also be included for providing power to the electronic processing unit 903.

One or two earphones 904 can be attached or embedded to the one or both eyeglass temples. The electronic processing unit will process the said digital or analogue signals and generate filtered, amplified analog signals which will be sent to earphone(s) 904. Two earphones can provide stereo sound to user.

The conductive wire(s) can be shared by multiple electronic signals, such as lens drive signals, the digital or analogue signal from the sensors, and output signals from the electronic processing unit to the earphones, after those signals will coded or modulated in space or frequency domain. Said signals may be separated by various filter means to make sure acoustic signals do not affect the electro-active lenses and that drive singles to the electro-active lenses do not affect the earphones.

The electronic processing unit 903 and power source can be enclosed in one or two application modules as described herein. The electronic processing unit 903 enclosed in the application module, or electronics module of the frame, can be programmed in order to adjust the sound quality and meet the different demands from different customers.

The inventive eyewear can also, by way of example only, comprise one or more of a vibrating means, energy or power source, microphone, speaker, sensor, docking station, memory down load mean, memory up load means, memory storage means, microprocessor, light or lights.

The eyewear can comprise a power source which can be, by way of example, one of a rechargeable battery, disposable battery, fuel cell, solar cell, kinetic energy source. The eyewear can comprise an electronic module which is integrated into the eyewear or temple such that the electronic module can comprise one or more of memory storage, electrical power, sensor, microprocessor. The electronic module can be connected to the universal cable which is illustrated in the attached.

The term application module as used herein to be any device when added to the inventive eyewear that provides one of an improvement, pleasure, or a benefit to or for a wearer of the eyewear.

The securing means of the inventive eyewear can be that of a strap, a temple, or temples that secure the eyewear to the head of the wearer. The inventive eyewear can be, by way of example only, one of goggles, dress eyeglasses, occupational eyeglasses, shooting eyeglasses, safety eyeglasses, sunglasses. The eyeglasses can comprise any prescription optical power lens including a plano optical power. The lenses can be of today's conventional static focus optics or newer optics having the ability to dynamically change focus such as by way of example only, electronic, fluid, mechanical, membrane or of a conventional static focus (meaning after fabrication the lens cannot alter its optical power). The sunglasses can be those of any tint such as, by way of example only, photochromic, electro-chromic and solid fixed tints.

The inventive docking system disclosed herein, (of the inventive eyewear also disclosed herein), can be integral with said eyewear, attached to said eyewear, partially or fully housed within said eyewear. The docking station can be located to the inside back of the frame or eyewear front, the outside of one of the temples or the inside of one of the temples. The docking station acts to secure a plurality of different application devices (one at a time or more than one at a time) to the eyewear and in some, but not all, cases provides one or more of electrical power, additional electrical power, memory down load capability, and memory upload capability. The eyewear's docking station provides the ability for one, two, three or more application devices to be docked simultaneously so as to provide the wearer with an optimal and most efficient hands free experience while wearing his or her inventive eyewear. The docking station is located such that when an application device module (which comprises a docking means) is docked a universal cable comprising audio, video, power and a microphone (mic) can be easily attached or connected to the application device module. The universal cable may be housed within the temple and attached directly or indirectly to one or more of a memory storage means, power means, sensor and microprocessor.

It should also be understood in certain embodiments the inventive docking station only comprises a means for physically securing application devices to the eye wear and enabling the routing of electrical power and information signals between said devices. In certain embodiments the docking station itself does not comprise any printed circuit boards that possess analog or digital circuitry. In other embodiments the inventive docking station comprises printed circuit boards possessing analog or digital circuitry. In still other embodiments of the invention the docking station is capable of docking a plurality of different application devices (either one at a time or simultaneously), whereby each application device comprises its own circuitry and logic such to control one of memory, power, an audio speaker, audio playback, or video playback, which is contained within the eyeglass frame. Certain of the illustrations which are incorporated are meant to show (but not labeled as such) this memory, power means, data, audio, video being incorporated within the electronic module housed within the temple. However, any one, a combination thereof or all of these features can be located anywhere within the eyewear or frame.

In some embodiments of the present technology, a water repellent material can be used to inhibit moisture and liquids from filling spaces between components of electro-active eyewear such as rimlock components. Electrically-insulating greases, such Dow Corning® 111 valve lubricant and sealant, can be useful in this regard. Electrically-insulating grease can be applied while the frame is being assembled. A syringe equipped with a soft plastic tip can be used for application.

According to an aspect of the present technology, one or more conductive wires can be embedded in the upper rim members, the bridge and/or the lower rim members of electro-active spectacles and frames of the present technology during a mold casting process. That is, when the upper rim members, the bridge and/or the lower rim members are formed using a casting process, one or more conductive wires can be cast over when the upper rim members, the bridge and/or the lower rim members are prepared. Generally, thicker conductive wires can be used during such a process. Nylon is an example material that can be used to mold over one or more conductive wires to from the upper rim members, the bridge and/or the lower rim members.

According to an aspect of the present technology, one or more conductive wires can be embedded in the upper rim members, the bridge and/or the lower rim members of electro-active spectacles and frames of the present technology as each frame component is assembled. More specifically, any of the upper rim members, the bridge and/or the lower rim members that will be used to embed one or more conductive wires can be fabricated by two or more individual or separate pieces. For example, the upper rim members can be formed from two substantially symmetrical pieces of substantially the same shape—a front piece and a back piece which individually may appear to be a portion of the upper rim member split in half lengthwise. Prior to assembling the front and back pieces to form a complete upper rim member, one or more wires can be embedded (e.g., in a groove formed by mold or machined into the front and/or back pieces) between the front and back pieces (i.e., at the interface between the front and back pieces). The front and back pieces used to form the complete upper rim member can subsequently be combined, for example, using an adhesive.

According to an aspect of the present technology, one or more conductive wires can be embedded in the upper rim members, the bridge and/or the lower rim members of electro-active spectacles and frames of the present technology after the frame is assembled. Specifically, one or more grooves can be machined into the upper rim members, the bridge and/or the lower rim members that can be used to contain one or more conductive wires. The machined grooves can then be filled or covered with material to cosmetically hide the conductive wires. The assembled frame can then be polished to hide or mask the area in which the wires are embedded. Acetate is an example material that can be manipulated in this fashion to embed one or more conductive wires.

In some embodiments, connections can be made from conductive compressible members. Conductive compressible members can include conductive rubber and metal rubber. Metal rubber is a name for conductive plastic polymers with metal ions, it is a self-assembling nano-composite, and is flexible and durable across a broad range of pressures, temperatures, tensions, exposure to chemicals. It retains its properties upon being returned to a ground state. It can carry data and electrical power.

In some embodiments, the conductive cable itself can be an insulating element.

While various embodiments of the present technology have been described above, it should be understood that they have been presented by way of example and not limitation. Any conductive element described above (e.g., the upper or lower portions of the frame) can be entirely conductive (and possibly coated with non-conductive material) or can contain an embedded or buried conductive element (e.g., a conductive core) and a non-conductive outer or surrounding layer. Further, any conductive link—e.g., described or referred to as an electrical wire or connection—could alternatively, or in addition thereto, be or include an optical conductive link as will be apparent to one skilled in the pertinent art. The exemplary techniques for coupling or connecting the electrical elements of the electro-active spectacles of the present technology (e.g., the controlling electronics and power supplies and electro-active lenses) using embedded conductive links can be used to embed one or more conductive optical links (e.g., one or more optical fibers) as will be apparent to one skilled in the pertinent art.

These applications can be that of, by way of example only, by way of example only, electronic focusing eyeglasses, electro-active eyeglasses, fluid lenses being activated by way of an electronic actuator, mechanical or membrane lenses being activated by way of electronics, electro-chromic lenses, electronic fast tint changing liquid crystal lenses, lenses whose tint can be altered electronically, lenses that by way of an electrical charge can resist or reduce the attraction of dust particles, lenses or eyeglass frames housing or having an electronic display affixed thereto, electronic eyewear providing virtual reality, electronic eyewear providing 3-D capabilities, electronic eyewear providing gaming, and electronic eyewear providing augmented reality.

Although many embodiments were described above as comprising different features and/or combination of features, a person of ordinary skill in the art after reading this disclosure may understand that in some instances, one or more of these components could be combined with any of the components or features described above. That is, one or more features from any embodiment can be combined with one or more features of any other embodiment without departing from the scope of the invention.

As noted previously, all measurements, dimensions, and materials provided herein within the specification or within the figures are by way of example only.

A recitation of "a," "an," or "the" is intended to mean "one or more" unless specifically indicated to the contrary.

As used herein, reference to a "first" or a "second" does not limit the referenced component to a particular location unless expressly stated. For instance, reference to a "first temple" may comprise the temple located on either the left side or the right side of a wearer's head.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

The invention claimed is:

1. Eyewear comprising:
    an eyewear frame having a first temple and a second temple;
    a speaker coupled to the eyewear frame; and
    an application module mechanically coupled to the eyewear frame and operably coupled to the speaker, the application module comprising:
        a microphone to receive a verbal query from a wearer of the eyewear; and
        a Bluetooth chip, operably coupled to the microphone and the speaker, to connect to a Bluetooth-enabled external device, to transmit the verbal query to the Bluetooth-enabled external device, to receive a response to the verbal query from the Bluetooth-enabled external device, and to provide the response to the wearer via the speaker,
wherein the verbal query causes the Bluetooth-enabled external device to obtain the response to the verbal query via the Internet by searching the Internet for the response to the verbal query.

2. The eyewear of claim 1, wherein the Bluetooth-enabled external device is configured to control an external audio device based at least in part on an instruction from the wearer.

3. The eyewear of claim 1, wherein the Bluetooth-enabled external device is configured to control an external video device based at least in part on an instruction from the wearer.

4. The eyewear of claim 1, wherein the Bluetooth-enabled external device is configured to control light and/or temperature in an environment of the wearer based at least in part on preferences of the wearer.

5. The eyewear of claim 1, wherein the application module further comprises:
a voice recognition chip operably coupled to the microphone and the Bluetooth chip.

6. A method comprising:
receiving, by a microphone mechanically coupled to an eyewear frame, a verbal query from a person wearing the eyewear frame;
transmitting, by a wireless chip mechanically coupled to the eyewear frame and operably coupled to the microphone, the verbal query to an external device, the verbal query causing the external device to search the internet for a response to the verbal query;
receiving, by the wireless chip, the response to the verbal query from the external device; and
providing the response to the verbal query to the person wearing the eyewear frame via a speaker operably coupled to the wireless chip.

7. The method of claim 6, wherein the verbal query is a query about weather and the response to the verbal query includes information about the weather.

8. The method of claim 6, wherein the wireless chip is a Bluetooth wireless chip, and further comprising:
pairing the Bluetooth wireless chip with the external device before transmitting the verbal query to the external device.

9. The method of claim 6, further comprising:
controlling light in an environment of the person wearing the eyewear frame based at least in part on preferences of the person wearing the eyewear frame.

10. The method of claim 6, further comprising:
controlling a temperature of an environment of the person wearing the eyewear frame based at least in part on preferences of the person wearing the eyewear frame.

11. The method of claim 5, wherein the external device is at least one of a cell phone, a smart phone, a computer, an iPad, and/or a tablet.

12. Eyewear comprising:
an eyewear frame having a first temple and a second temple; and
an application module mechanically coupled to the eyewear frame and operably coupled to a speaker, the application module comprising:
a microphone to receive a verbal query from a wearer of the eyewear; and
a processor, operably coupled to the microphone and the speaker, to transmit the verbal query to an external device, receive a response to the verbal query from the external device, and provide the response to the wearer via the speaker,
wherein the verbal query causes the external device to obtain the response to the verbal query by searching the Internet for the response to the verbal query.

13. The eyewear of claim 12, wherein the external device is a smart phone.

14. The eyewear of claim 13, wherein the application module further comprises a wireless chip, operably coupled to the processor, to wirelessly transmit the verbal query to the external device.

15. The eyewear of claim 14, wherein the wireless chip is a Bluetooth chip.

16. The eyewear of claim 12, wherein the external device is a computer.

17. The eyewear of claim 12, wherein the verbal query includes a query about the weather.

18. The eyewear of claim 17, wherein a response to the query includes information about the weather.

19. The eyewear of claim 12, wherein the external device is configured to control an external audio device based at least in part on an instruction from the wearer.

20. The eyewear of claim 12, wherein the external device is configured to control an external video device based at least in part on an instruction from the wearer.

* * * * *